(12) United States Patent
Zabeau et al.

(10) Patent No.: US 7,026,115 B1
(45) Date of Patent: *Apr. 11, 2006

(54) SELECTIVE RESTRICTION FRAGMENT AMPLIFICATION: FINGERPRINTING

(75) Inventors: Marc Zabeau, Ghent (BE); Pieter Vos, Renkum (NL)

(73) Assignee: Keygene N.V., Wageningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 08/769,450

(22) Filed: Dec. 19, 1996

Related U.S. Application Data

(60) Division of application No. 08/180,470, filed on Jan. 12, 1994, now Pat. No. 6,045,994, which is a continuation of application No. 07/950,011, filed on Sep. 24, 1992, now abandoned.

(30) Foreign Application Priority Data

Sep. 24, 1991 (EP) .................................. 91402542

(51) Int. Cl.
*C12Q 1/68* (2006.01)
*C12P 19/34* (2006.01)
*C07H 21/04* (2006.01)

(52) U.S. Cl. ...................... 435/6; 435/91.2; 536/24.2; 536/24.33

(58) Field of Classification Search .................... 435/6, 435/91.2; 536/24.2, 24.33
See application file for complete search history.

(56) References Cited

U.S. PATENT DOCUMENTS

| | | | | |
|---|---|---|---|---|
| 4,321,365 A | | 3/1982 | Wu et al. ...................... 536/27 |
| 4,683,195 A | * | 7/1987 | Mullis et al. ................... 435/6 |
| 5,093,245 A | | 3/1992 | Keith et al. .................... 435/91 |
| 5,366,877 A | | 11/1994 | Keith ......................... 435/91.2 |
| 5,487,985 A | | 1/1996 | McClelland et al. | |
| 6,045,994 A | * | 4/2000 | Zabeau et al. .................. 435/6 |
| 6,228,608 B1 | * | 5/2001 | Young et al. ............... 435/69.1 |

FOREIGN PATENT DOCUMENTS

| | | |
|---|---|---|
| CA | 2 036 946 | 10/2001 |
| WO | 90/08821 | 8/1990 |
| WO | 90/11372 | 10/1990 |
| WO | 91/05861 | 5/1991 |
| WO | 91/14001 | 9/1991 |
| WO | 91/14003 | 9/1991 |
| WO | WO 91/13075 | 9/1991 |
| WO | 92/07095 | 4/1992 |
| WO | 92/13104 | 8/1992 |

OTHER PUBLICATIONS

Straus et al. Genomic substraction for cloning DNA corresponding to deletion mutations. Proc. Natl. Acad. Sci. USA. vol. 87, p. 1889-1893, 1990.*
New England Biolabs, Primers and Probes, New England Biolabs catalog, p. 54-55, 1986/87.*
*Oxford University Press*, "Genomic Walking and Sequencing by Oligo-Cassette Mediated Polymerase Chain Reaction", vol. 18, No. 10, pp. 3095-3096, 1990.
"Direct Cloning and Sequence Analysis of Enzymatically Amplified Genomic Sequences", *Science*, Scharf, S.J., et al., Sep. 5, 1986, vol. 233, pp. 1076-1078.
*Nucleic Acids Research*, "Arbitarily Primed PCR Fingerprinting of RNA", J. Welsh et al., vol. 20, No. 19, pp. 4965-4970, 1992.
*Anal. Chem.*, "DNA Amplification by the Polymerase Chain Reaction", Richard A. Gibbs, vol. 62, pp. 1202-1214, 1990.
*Nucleic Acids Research*, "DNA Polymorphisms Amplified by Arbitrary Primers are Useful as Genetic Markers", J. Williams, et al., vol. 18, No. 22, pp. 6531-6535, 1990.
"Effects of Primer—template mismatches on the polymerase chain reaction . . . ", S. Kwok et al., *Nucleic Acids Records*, vol. 18, No. 4, 1989.
"Analysis of any point mutation in DNA. The amplification refractory mutation system (A ARMS)", C.R. Newton et al., *Nucleic Acids Records*, vol. 17, No. 7, 1989.

(Continued)

*Primary Examiner*—Kenneth R. Horlick
*Assistant Examiner*—Joyce Tung
(74) *Attorney, Agent, or Firm*—Buchanan Ingersoll PC

(57) ABSTRACT

The invention relates to a process for the controlled amplification of at least one part of a starting DNA containing a plurality of restriction sites for a determined specific restriction endonuclease, and of which at least part or its nucleic acid is unknown.

Application of this process to human, animal or plant DNA fingerprinting, to identification of restriction fragment length polymorphisms.

Kit for the application of the process.

11 Claims, 18 Drawing Sheets

OTHER PUBLICATIONS

Dennis E. Schwartz et al., "*Rous sarcoma* virus genome is terminally redundant: The 3' sequence," Proc. Natl. Acad. Sci. USA, vol. 74, No. 3, pp. 994-998, Mar. 1977.

L. Fugger et al., "Technical aspects of typing for HLA-DP alleles using allele-specific DNS in vitro amplification and sequence-specific oligonucleotide probes," Journal of Immunological Methods, vol. 129, pp. 175-185, 1990.

M.S.H. Ko et al., "Unbiased amplification of a highly complex mixture of DNA fragments by 'lone linker'—tagged PCR," Nucleic Acids Research, vol. 18, No. 14, pp. 493-494, 1990.

Nature, vol. 387, Supplement, May 29, 1997.

List of Publications obtained from Science Citation Index (ISI) online database from STN Scisearch database.

* cited by examiner

Fig. 2 adaptor ligation

Fig. 4 Multiplex restriction fragment amplification

Fig. 6 Selective PCR amplification of restr. fr.

Fig. 7 Selective restriction fragment amplification

Fig. 8 Fragment specific selective PCR primers

Fig. 9 Principle of ARF

SRFA OF FOUR TOMATO LINES USING PSTI AND MSEI AS RESTRICTION ENZYMES

|01|02|03|04|05|06|07|08|09|10|11|12|13|14|15|16|17|18|19|20|21|22|23|24|25|26|27|28|

SRFA OF LACTUCA DNAs USING PSTI AND MSEI AS RESTRICTION ENZYMES

SRFA OF CORN DNAs USING PSTI/TAQI AND ECORI/TAQ1

SRFA OF BACTERIAL DNAs USING APAI AND TAQ1 AS RESTRICTION ENZYMES

SRFA OF ANIMAL DNAs USING SSE83871 AND MSEI AS RESTRICTION ENZYMES

SELECTIVE RESTRICTION FRAGMENT AMPLIFICATION: FINGERPRINTING

This application is a divisional, of application Ser. No. 08/180,470, filed Jan. 12, 1994, now U.S. Pat. No. 6,045,944 which is a continuation of application Ser. No. 07/950,011, filed Sep. 24, 1992, now abandoned.

BACKGROUND OF THE INVENTION

1. Field of the Invention

This invention relates to applications of DNA fingerprinting and the use of DNA markers in a number or different fields including, but not limited to, plant and animal breeding, variety or cultivar identification, diagnostic medicine, disease diagnosis in animals and plants, identification of genetically inherited diseases in humans, family relationship analysis, forensic analysis, and microbial typing.

More specifically, this invention relates to methods for DNA fingerprinting and for detecting specific DNA markers in genomes ranging from microorganisms to higher plants, animals and humans. The invention also relates to synthetic DNA molecules and products based thereon which are used in the methods of the invention in the different fields of application.

2. Description of the Related Art

1. DNA fingerprinting

DNA fingerprinting or DNA typing, as well as other methods of genotyping profiling and DNA identification analysis, refer to the characterization of either similarities or one or more distinctive features in the genetic make up or genome of an individual, a variety or race, or a species. The general rule is that the closer the genetic relationship is, the greater the identity or more appropriate the similarity of genomes, and consequently distinctive features in the genome will be rarer. These similar or distinctive features can be revealed by analyzing the DNA of an organism after cleaving the DNA with a restriction endonuclease. Restriction endonucleases are enzymes which recognize short nucleotide sequences, usually 4 to 8 bases in length and cleave the two DNA strands, thereby producing fragments of DNA of discrete length. Because of their high degree of sequence specificity, restriction endonucleases will cleave DNA molecules in a very specific fashion. The result is that a reproducible set of DNA fragments will be produced. DNA fragments can be fractionated according to their length on porous matrices, or gels, yielding typical banding patterns, which constitutes a DNA fingerprint of the organism's genetic makeup.

2. DNA polymorphisms

When the fingerprints of very closely related species, varieties or races are compared, the DNA fingerprints can be identical or very similar. When differences are observed within otherwise identical DNA fingerprints, such differences are referred to as DNA polymorphisms: these are new DNA fragments which appear in a fingerprint. The DNA is said to be polymorphic at that position and the novel DNA fragment can be used as a DNA marker. DNA polymorphisms detected in DNA fingerprints obtained by restriction enzyme cleavage can result from any of the hollowing alterations in the DNA sequence: mutations abolishing the restriction endonuclease target site, mutations creating new target sites, insertions, deletions or inversions between the two restriction sites.

Such DNA polymorphisms are generally referred to as RFLP, Restriction Fragment Length Polymorphisms. Such mutational changes will behave as bona fide genetic markers when they are inherited in a mendelian fashion. Consequently, DNA polymorphisms can be used as genetic markers in much the same way as other generic markers: in parentage analysis, in genetic studies on the inheritance of traits, or in the identification of individuals.

3. DNA fingerprinting techniques

For almost all living organisms, except viruses, restriction digests of the total genomic DNA of the organisms yield so many bands that it is not possible to score individual bands. Therefore, all methods for DNA fingerprinting are based on the principle that only a small fraction of the DNA fragments are visualized so as to yield a simple banding pattern which constitutes the DNA fingerprint.

The most widely utilized method involves digesting the DNA of the organism with restriction endonucleases, fractionating the restriction fragments by gel electrophoresis, transferring and binding the fractionated DNA fragments onto membranes and hybridizing the membrane with a specific DNA fragment ("probe"). The DNA fragment will form double-stranded DNA molecules with the DNA fragment (or fragments) on the membrane which has (have) complementary nucleotide sequences. When the probe is tagged with a visualizable marker, the DNA fragment to which the probe is attached can be visualized. This procedure is generally referred to as "Southern hybridization". When differences are observed in the sizes of the corresponding restriction fragments to which the probe attaches in closely related genomic DNA molecules, these differences are referred to as DNA polymorphisms, more specifically restriction fragment length polymorphisms. The restriction fragment length differences correspond to the different allelic forms of the genetic locus recognized by the DNA probe. Although the Southern hybridization method for DNA fingerprinting has been widely used, the method is laborious and time consuming.

Furthermore, the method has a low resolution and can thus only be used to score single loci or a few loci at most in a single reaction.

4. Polymerase chain reaction

The Polymerase Chain Reaction (PCR) technique is a method for synthesizing specific DNA fragments in vitro. The method relies on the use of specific oligonucleotides which will attach to unique sequences on a DNA molecule and a thermostable DNA polymerise. The oligonucleotides are designed in such a way that they can anneal to the opposite strands of the DNA and serve as primers in a DNA synthesis reaction in such a way that each will direct the synthesis of new DNA strands. Hence, in one round of synthesis a complete copy of the DNA molecule between the primers will be made, so that the DNA between the primers is duplicated. Each round of DNA synthesis results in the doubling of the amount of DNA, hence leading to the amplification of the DNA comprised between the two primers. Consequently, the PCR technique allows one to synthesize a precise DNA segment using a small amount of "substrate DNA".

SUMMARY OF THE INVENTION

In the present invention we have devised a new method to amplify, with the PCR method, restriction fragments obtained after cleaving the DNA of an organism with at least one restriction enzyme. In this novel application of the PCR method the oligonucleotides used are not directed against a known DNA sequence but are designed such that they recognize the ends of the restriction fragments. To this end it is necessary to modify the ends of the restriction fragments by adding oligonucleotide linkers (or adaptors) to the ends. The reason for this is that the ends of restriction enzymes have only usually few nucleotides in common, i.e. 2 to 8 nucleotides, too short to be used to design primers for PCR amplification.

The invention is based on the use of a novel application of polymerase chain reaction technique (PCR) for amplifying one or more restriction fragments from complex mixtures of DNA fragments obtained by digesting genomic DNA molecules with restriction endonucleases. One particular advantage of the invention is to enable the amplification of DNA restriction fragments in situations where the nucleotidic sequence of the ends of the restriction fragments are not determined. In such cases the usual sequence specific primers hybridizing to each strand of a restriction fragment to be amplified can not be defined and therefore one cannot use the methods known in the art for amplification purposes.

The method of the invention can be used for instance in two different ways, leading to two different types of applications:

(1) Methods for DNA fingerprinting of gnomes by randomly selecting subsets of one or more restriction fragments to be amplified by the PCR technique. The invention also covers synthetic oligonucleotides for use in said methods and some applications of said methods can be forensic typing, microbial identification, varietal identification, pedigree analysis and screening of DNA markers linked to genetic traits;

(2) Methods for identifying one or more preselected DNA fragments which can be polymorphic, by PCR amplification. The invention also covers specific synthetic oligonucleotides for use in said methods and some applications of said methods can be the screening of genetically inherited diseases in humans, monitoring the inheritance of agronomic traits in plant and animal breeding and the detection of infections agents in diseases.

DETAILED DESCRIPTION OF THE INVENTION

Definitions

Figure 1:
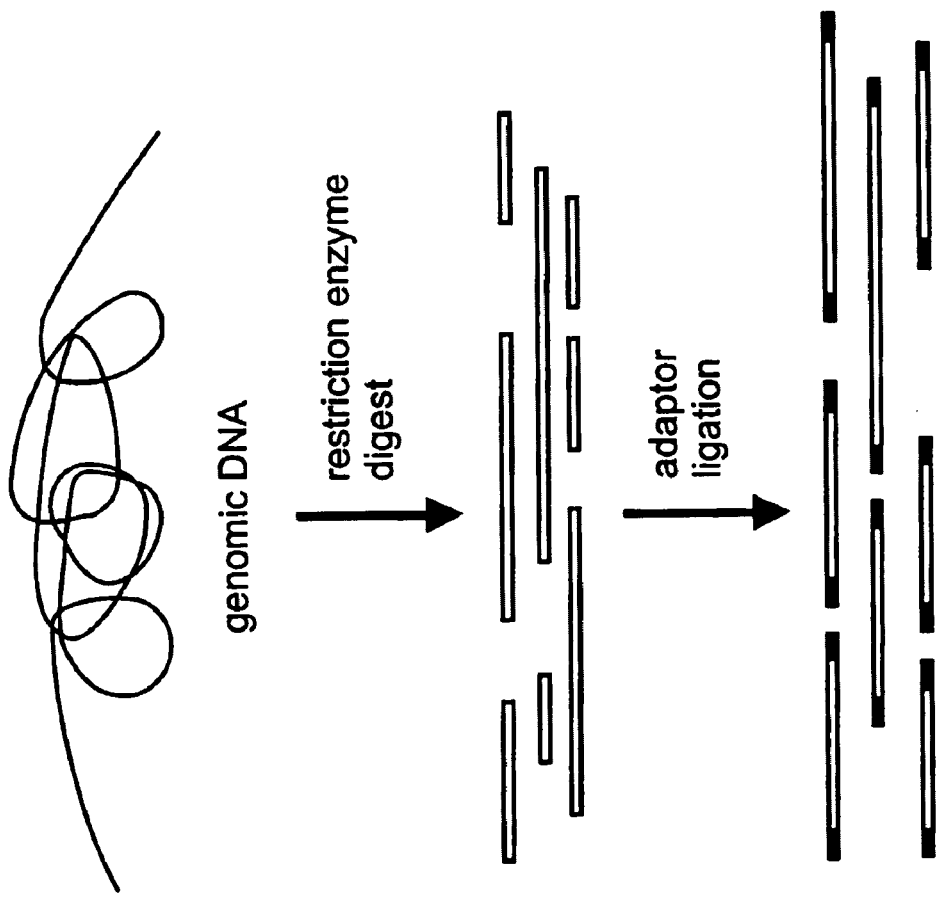
FIG. 1 provides a graphic outline for tagged restriction fragments by digesting genomic DNA molecules with a restriction enzyme and subsequent ligation of adaptors.

In the description and examples that follow, a number of terms are used herein. In order to provide a clear and consistent understanding of the specification and claims, including the scope to be given such terms, the following definitions are provided.

Restriction Endonuclease: a restriction endonuclease or restriction enzyme is an enzyme that recognizes a specific base sequence (target site) in a double-stranded DNA molecule, and will cleave both strands of the DNA molecule at every target site.

Restriction Fragments: the DNA molecules produced by digestion with a restriction endonuclease are referred to as restriction fragments. Any given genome will be digested by a particular restriction endonuclease into a discrete set of restriction fragments. The DNA fragments that result from restriction endonuclease cleavage are separated and detected by gel electrophoresis.

Restriction Fragment Length Polymorphism (RFLP): the genomic DNA of two closely related organisms, for example, will exhibit differences in their nucleotide sequence composition at many sites. When these differences occur in the target site for a restriction endonuclease, the modified target site will not be cleaved at that point. Likewise, a nucleotide sequence variation may introduce a novel target site where none exists in the other organism, causing the DNA to be cut by the restriction enzyme at that point. Alternatively, insertions or deletions of nucleotides occurring in one organism between two target sites for a restriction endonuclease will modify the distance between those target sites. Because of this, digestion of the two organism's DNA will produce restriction fragments having different lengths. A polymorphism in the length of restriction fragments produced by digestion of the DNA of the two organisms will result.

Gel Electrophoresis: To detect restriction fragments, an analytical method for fractioning double-stranded DNA molecules on the basis of size is required. The most commonly used technique for achieving such fractionation is gel electrophoresis. The rate at which DNA fragments move in such gels depends on their size; thus, the distances travelled decrease as the fragment lengths increase. The DNA fragments fractionated by gel electrophoresis can be visualized directly by a staining procedure if the number of fragments included in the pattern is small.

Synthetic oligonucleotides: the single-stranded DNA molecules having preferably from almost 10 to almost 50 bases, which can be synthesized chemically are referred to as synthetic oligonucleotides. In general, those synthetic DNA molecules are designed to have a unique nucleotide sequence, although it is possible to synthesize families of molecules having related sequences and which have different nucleotide compositions at specific positions within the nucleotide sequence. The term synthetic oligonucleotide will be used to refer to DNA molecules having a unique nucleotide, sequence. The term mixed synthetic oligonucleotides will be used to refer to families of related synthetic oligonucleotides.

Ligation: the enzymatic reaction catalyzed by the enzyme ligase in which two double-stranded DNA molecules are covalently joined together is referred to as ligation. In general, both DNA strands are covalently joined together, but it is also possible to prevent the ligation of one of the two strands, through chemical or enzymatic modification of one of the ends. In that case the covalent joining will occur in only one of the two DNA strands.

Adaptors: short double-stranded DNA molecules, with a limited number of base pairs, e.g. 10 to 30 base pairs long, which are designed in such a way that they can be ligated to the ends of restriction fragments. Adaptors are composed of two synthetic oligonucleotides which have nucleotide sequences which are in part complementary to each other. When mixing the two synthetic oligonucleotides, they will form a double-stranded structure in solution under appropriate conditions. One of the ends of the adaptor molecule is designed so that it can be ligated to the end of a restriction fragment, the other end is designed so that it cannot be ligated.

Polymerase Chain Reaction (PCR): the enzymatic reaction in which DNA fragments are synthesized from a substrate DNA in vitro is referred to as PCR. The reaction involves the us of two synthetic oligonucleotides, which are complementary to nucleotide sequences in DNA molecules which are separated by a short distance of a few hundred to a few thousand base pairs, and the use of a thermostable DNA polymerase. The chain reaction consists for example of a series of 10 to 30 cycles. In each cycle the substrate DNA is first denatured at high temperature. After cooling down the synthetic oligonucleotides which are present in vast excess will form double-stranded structures with the substrate DNA molecules in solution at specific sites on the substrate DNA molecule that have complementary nucleotide sequences. The oligonucleotide-substrate DNA complexes will then serve as initiation sites for the DNA synthesis reaction catalyzed by the DNA polymerase, resulting in the synthesis of a new DNA strand complementary to the substrate DNA strand.

DNA amplification: the term DNA amplification will be used to denote the synthesis of double-stranded DNA molecules in vitro using Polymerase Chain Reaction (PCR). The products of the PCR reaction will be referred to as amplified DNA fragments.

Primers: in general, the term primer refers to a DNA strand which can prime the synthesis of DNA. DNA polymerase cannot synthesize DNA de novo without primers; DNA polymerase can only extend an existing DNA strand in a reaction in which the complementary strand is used as a template to direct the order of nucleotides to be assembled. We will refer to the synthetic oligonucleotide molecules which are used in the PCP reaction as primers.

Southern Hybridization Procedure: the purpose of the southern hybridization procedure, also referred to as Southern blotting, is to transfer physically DNA fractionated by agarose gel electrophoresis onto a support such as nylon membrane or nitrocellulose filter paper while retaining the relative positions of DNA fragments resulting from the fractionation procedure. The methodology used to accomplish the transfer from agarose gel to the support is to draw the DNA from the gel into the support by capillary action.

Nucleic Acid Hybridization: Nucleic acid hybridization is used to detect related DNA sequences by hybridization of single-stranded DNA on supports such as nylon membrane or nitrocellulose filter papers. Nucleic acid molecules that have complementary base sequences will reform the double-stranded structure if mixed in solution under the proper conditions. The double-stranded structure will be formed between two complementary single-stranded nucleic acids even if one is immobilized on a support. In the Southern hybridization procedure, the latter situation occurs.

Hybridization Probe: to detect a particular DNA sequence in the Southern hybridization procedure, a labelled DNA molecule or hybridization probe is reacted to the fractionated DNA bound to a support such as nylon membrane or nitrocellulose filter paper. The areas on the filter that carry DNA sequences complementary to the labelled DNA probe become labelled themselves as a consequence of the reannealing reaction. The areas of the filter that exhibit such labelling can then be detected according to the type of label used. The hybridization probe is generally produced by molecular cloning of a specific DNA sequence form the maize genome.

This invention relates more particularly to a process and means which enable the polymerase chain reaction (PCR) be applicable to the detection of restriction fragment polymorphisms (RFPs) including length polymorphisms. This invention comprises methods for detecting RFPS, synthetic oligonucleotides for use in the methods of the invention, kits comprising means for detecting RFPs, and applications of the methods and procedures of the invention far plant and animal breeding, diagnostics of genetically inherited diseases, identification of organisms, and forensic typing, etc. . . .

Specifically, this invention provides means for the identification of either individual genomic restriction fragments or of sets of genomic restriction fragments from any organism, microorganism, plant, animal or human, which are either individually genetically linked to one or more particular traits or that collectively provide a fingerprint of the genome that can be used to identify an organism, a variety or an individual.

The general method of the invention for production and for identification of restriction fragments involves the use of restriction endonucleases, ligation of synthetic oligonucleotides to the restriction fragments, and FCR amplification of restriction fragments. Restriction endonucleases cleave genomic. DNA molecules at specific sites, target sites, thereby generating restriction fragments.

PCR amplification of restriction fragments no matter whether one knows the nucleotidic sequence of the ends of the restriction fragments or not, can be achieved according to the invention, by first ligating synthetic oligonucleotides (adaptors) to the ends, of restriction fragments, thus providing each restriction fragment with two common tags which will serve as a anchor base for the primers used in PCR amplification.

Figure 2:
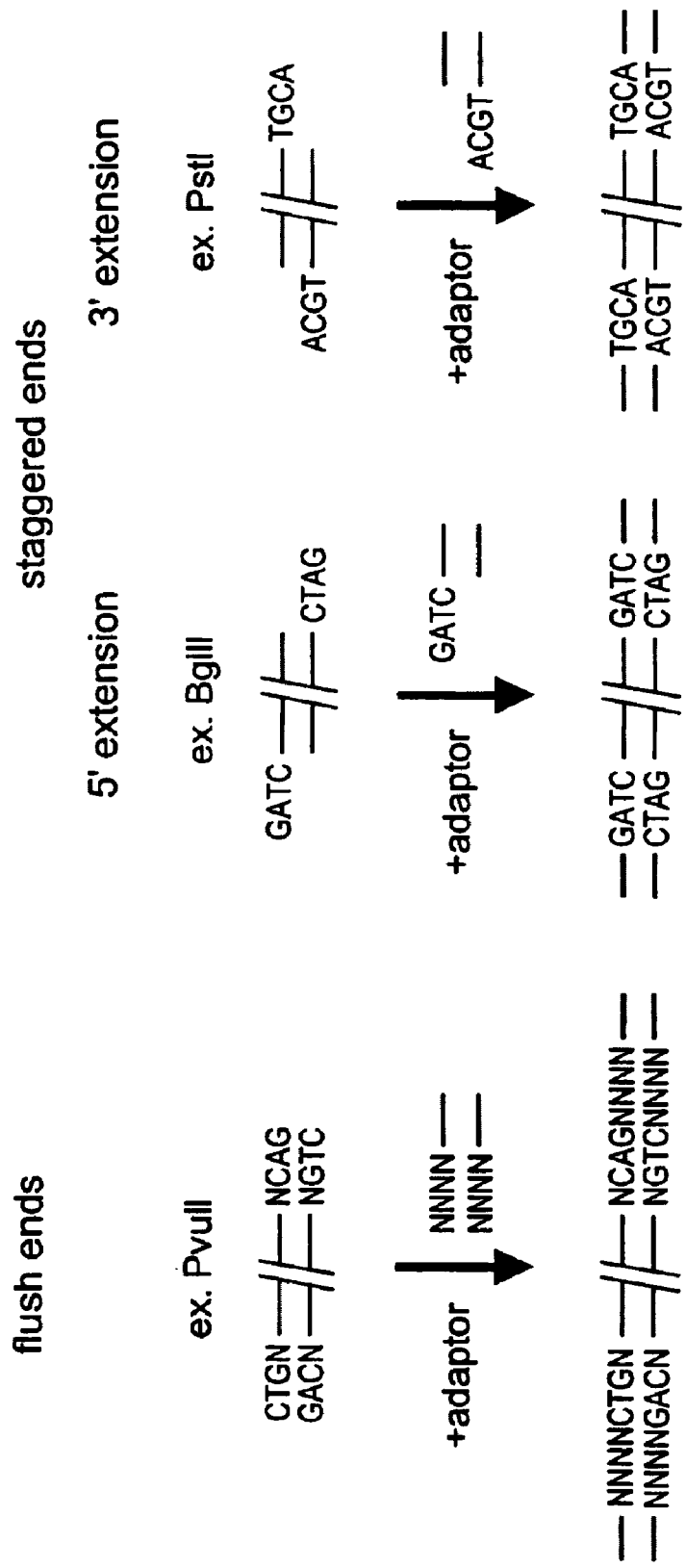
FIG. 2 depicts the ligation of adaptors to different ends of restriction fragments; flush ends and staggered ends.

Typically, restriction enzymes produce either flush ends, in which the terminal nucleotides of both strands are base paired, or staggered ends in which one of the two strands protrudes to give a short single strand extension (FIG. 2). In the case of restriction fragments with flush ends, adaptors are used with one flush end. In the case of restriction fragments with staggered ends adaptors are used which have a single stranded extension which is complementary to the single stranded extension of the restriction fragment. Consequently, for each type of restriction fragment specific adaptors are used, which differ in one of the ends so as to allow the adaptor to be ligated to the restriction fragment. Typically, the adaptors used are composed of two synthetic oligonucleotides which are in part complementary to each other, and which are usually approximately 10 to 30 nucleotides long, preferably 12 to 22 nucleotides long and which form double-stranded structures when mixed together in solution. Using the enzyme ligase the adaptors are ligated to the mixture of restriction fragments. When using a large molar excess of adaptors over restriction fragments one ensures that all restriction fragments will end up carrying adaptors at both ends. Restriction fragment prepared with this method will be referred to as tagged restriction fragments and the method will be further referred to as restriction fragment tagging.

Figure 3:
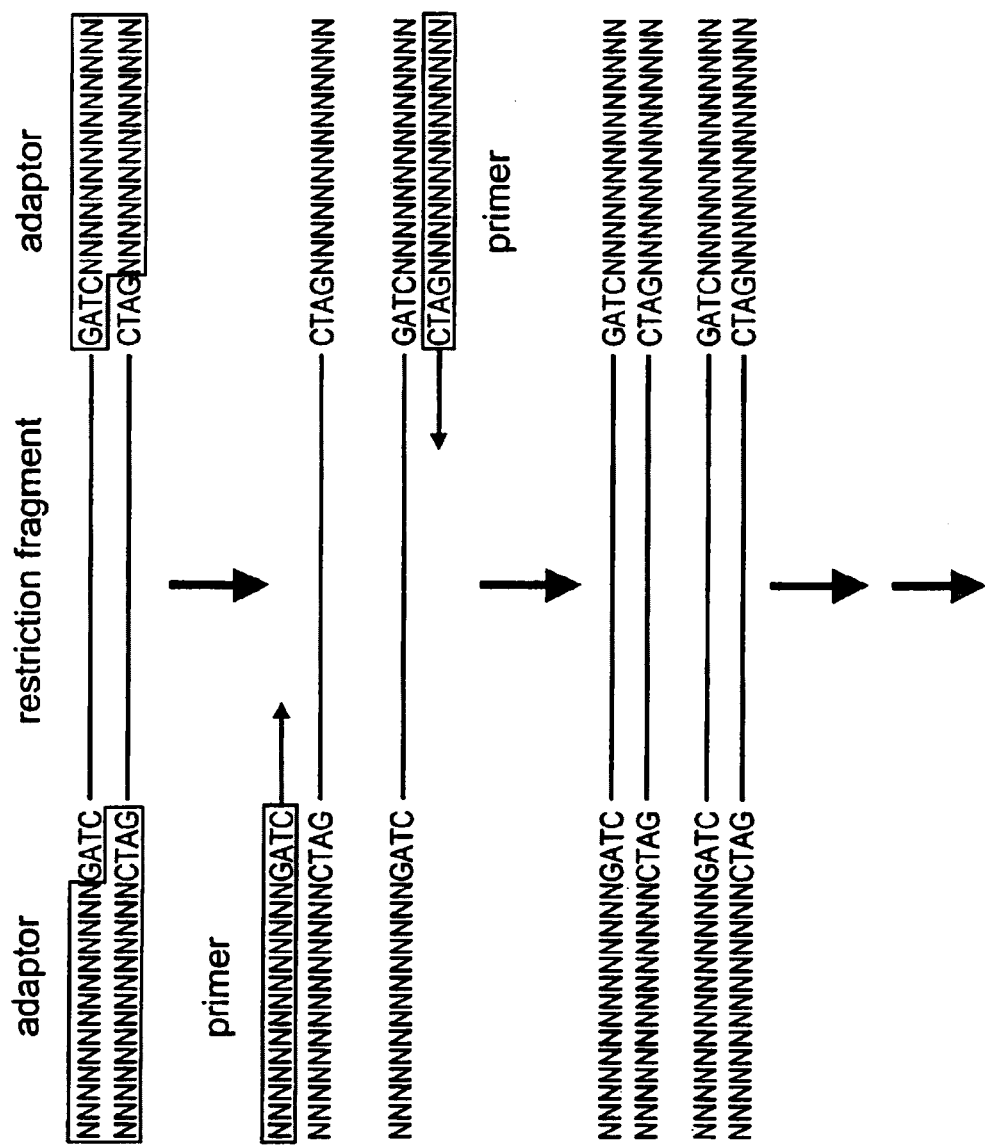
FIG. 3 (SEQ ID NO:68–72) depicts the PCR amplification of tagged restriction fragments. The boxed areas depict the adaptors which are ligated to the restriction fragment, and the primers which are used in the PCR amplification. The arrows indicate the direction of DNA synthesis.
Figure 4:
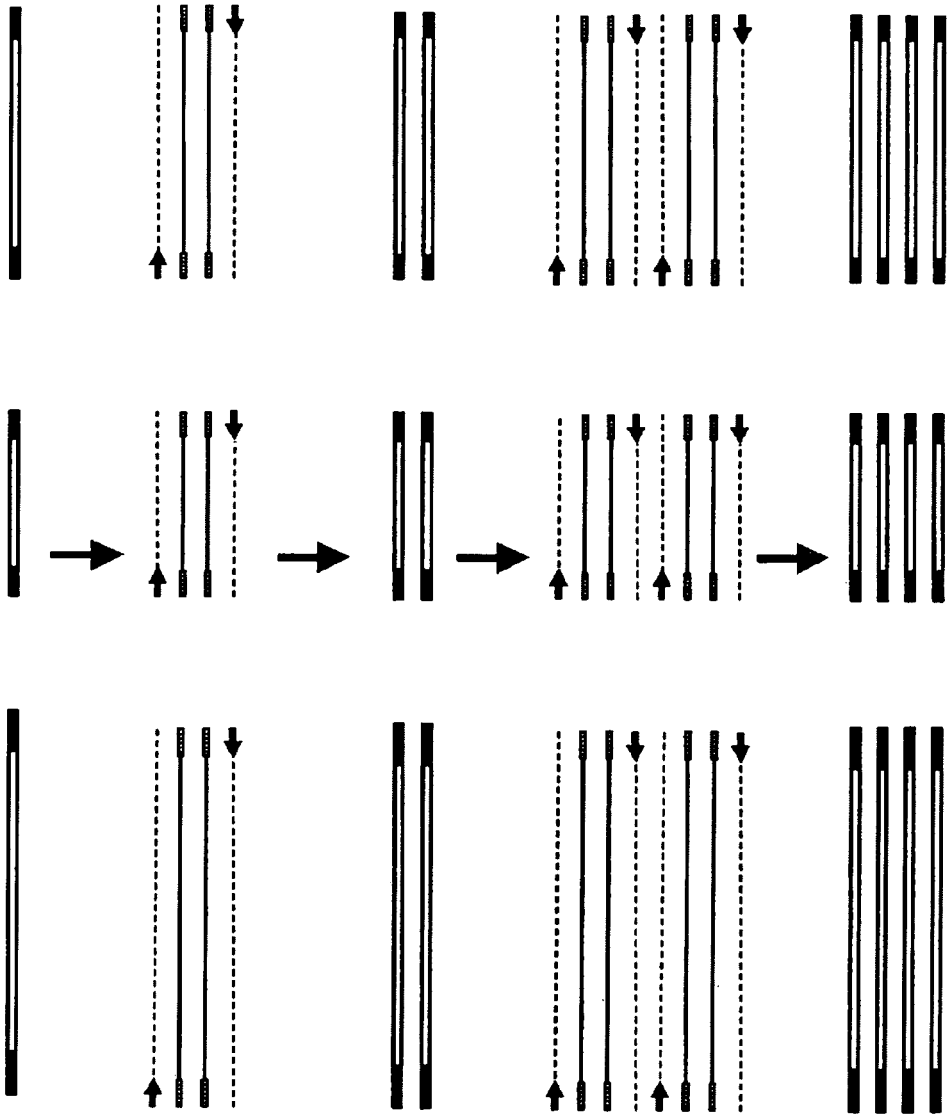
FIG. 4 provides a graphic outline for the PCR amplification of tagged restriction fragments.

The adaptors can now serve as templates for the primers having the characteristics hereabove defined, used in the subsequent PCR amplification reaction. In a preferred embodiment of the invention, the restriction fragment carries the same adaptor at both of its ends and a single PCR primer can be used to amplify the restriction fragment as illustrated in FIG. 3. Since in such a case all restriction fragments are tagged in the same way, it is obvious that PCR amplification of a mixture of tagged restriction fragments will amplify all restriction fragments in a synchronous fashion. In another embodiment using two different restriction enzymes to cleave the DNA, two different adaptors are ligated to the ends of the restriction fragments. In this case two different PCR primers can be used to amplify such restriction fragments. In another preferred embodiment using two restriction enzymes the adaptor for one of the enzyme ends is biotinylated. This allows one to select out of the complex mixture of restriction fragments those restriction fragments carry at least one end for this restriction enzyme, using usual methods for isolating biotinylated molecules. This step reduces the complexity of the starting mixture of restriction fragments and constitutes an enrichment step prior to the PCR amplification, thereby reducing in certain instances the background. The simultaneous amplification of several different fragments is often referred to as multiples PCR. The principle of multiplex restriction fragment amplification is illustrated in FIG. 4.

The present invention is further based on the definition of specifically designed primers and specific methods to direct the PCR amplification reaction in such a way that a controlled amplification is possible and in a particular embodiment of the invention, in such a way that only a small subset of tagged restriction fragments is amplified.

In general, restriction endonuclease digests or genomic DNA, and in particular of animal, plant or human genomic DNA, yields very large numbers of restriction fragments. The number of restriction fragments depends upon the size of the genome and of the frequency of occurrence of the target site of the restriction endonuclease in the genome which in turn is primarily determined by the number of nucleotides in the target site. The number of nucleotides in the target sites of commonly used restriction endonucleases ranges from 4 to 8. The genome sizes of organisms vary widely from a few million base pairs in the case of microorganisms to several billion base pairs for animals and plants. Hence, the number of restriction fragments obtained after cleaving genomic DNA molecules with a restriction enzyme can vary from a few hundred to several million. Generally, the number of restriction fragments is so large that it is not possible to identify individual restriction fragments in genomic DNA digests fractionated by gel electrophoresis. Such digests usually produce a smear of bands.

PCR amplification of tagged restriction fragments should thus also produce a smear of bands since all fragments should coamplify synchronously in the PCR reaction in a preferred embodiment of the invention applicable to genomic DNAs of large sizes, we have used a general principle to limit the number of restriction fragments which are to be amplified. This is done by preselecting a subset of tagged restriction fragments so that only a relatively small number of tagged restriction fragments will be amplified during the PCR amplification reaction.

Figure 5:
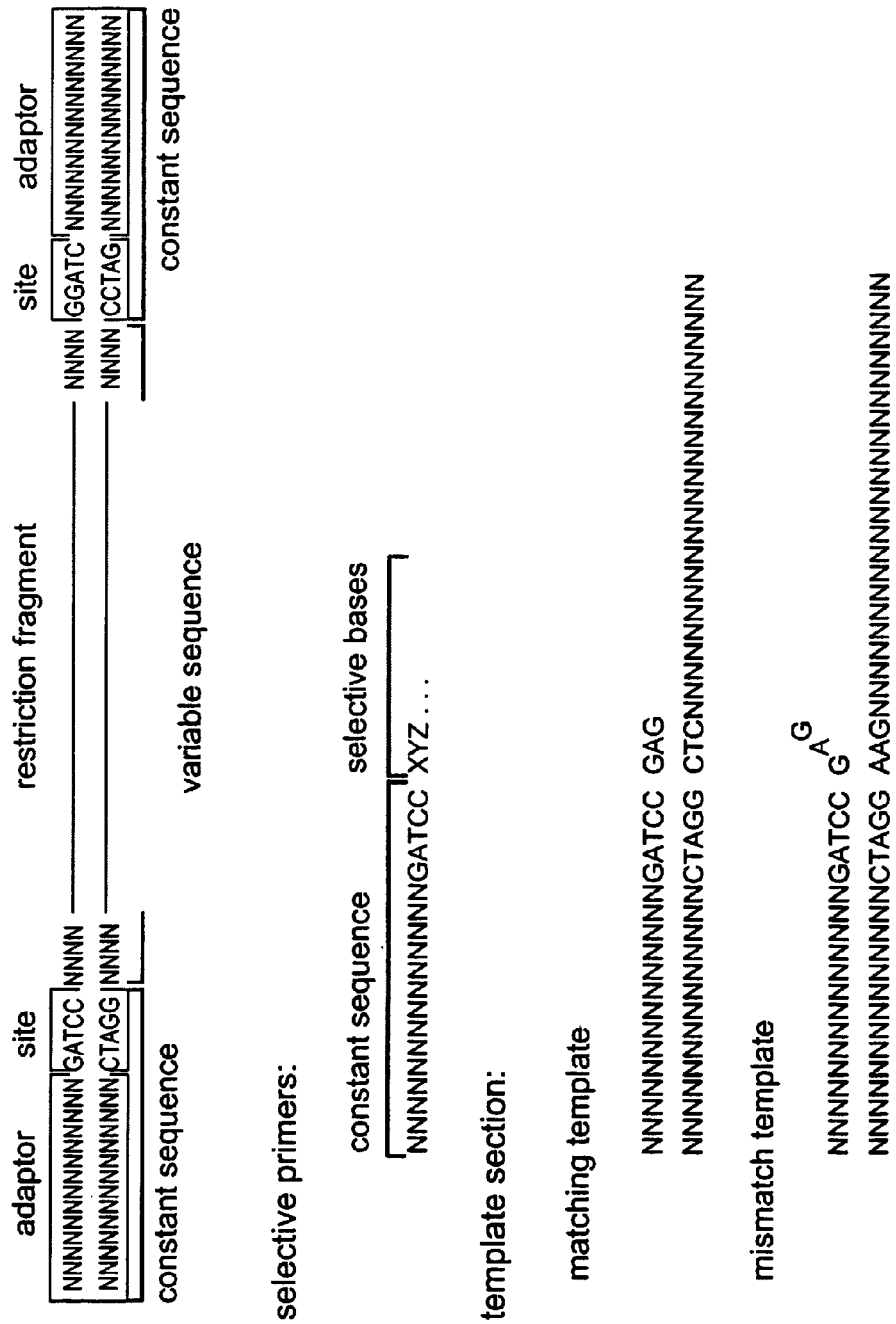
FIG. 5 (SEQ ID NO:73–78) shows the general design of the selective primers used in the PCR amplification of tagged restriction fragments. The boxes denote the constant sequences at the ends of the restriction fragments. The selectivity of the primers is illustrated in two examples where there is respectively a perfect match and a total mismatch between the selective base sequence and that of the restriction fragment template DNA.
Figure 6:
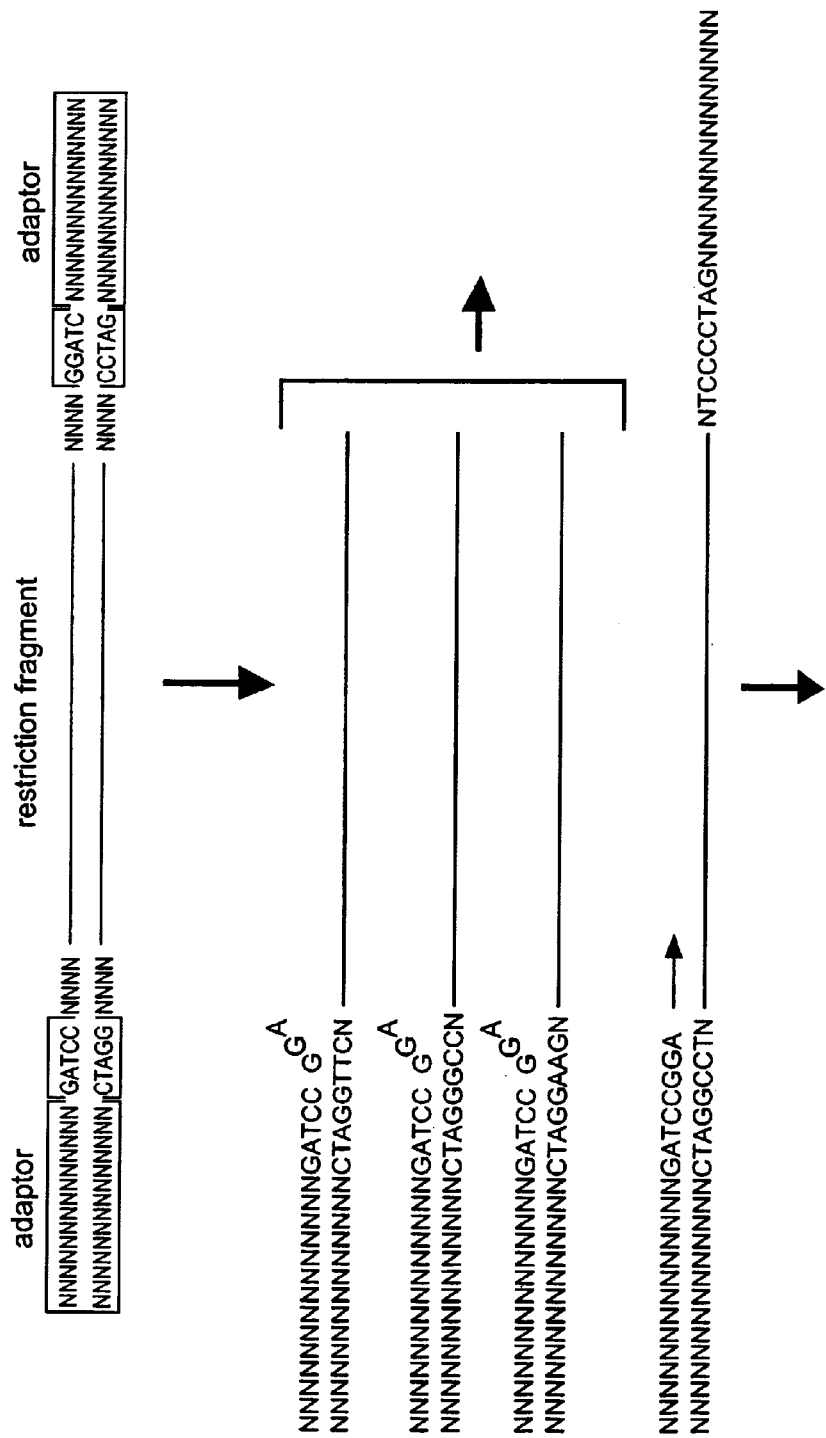
FIG. 6 (SEQ ID NO:79–83) shows the principle of selective PCR amplification using a PCR primer which selects template DNA molecules having a trinucleotide sequence adjacent to the adaptor sequence.
Figure 7:
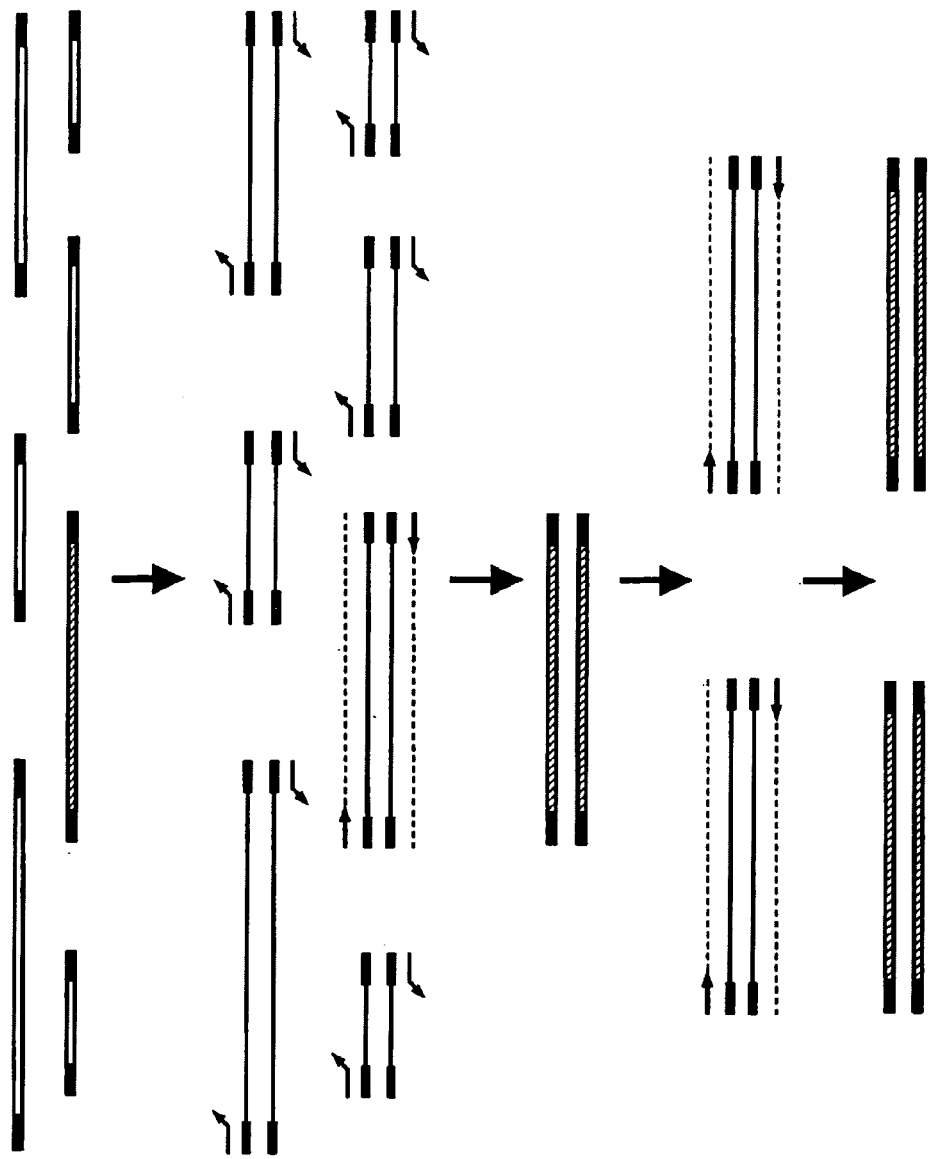
FIG. 7 depicts the selective PCR amplification of tagged restriction fragments.

The selective principle defined in this embodiment of the invention resides in the design of the oligonucleotides which are used as primers for the PCR amplification, as is illustrated in FIG. 5.

Tagged restriction fragments have the following general structure: a variable DNA sequence (corresponding to the restriction fragment before tagging), flanked on both sides by a constant sequence. The inverted DNA sequence (constant DNA sequence) is composed or part of the target sequence or the restriction endonuclease and of the sequence of the adaptor attached to both ends of the restriction fragment. The variable sequences of the restriction fragments comprised between the constant DNA sequences are usually unknown, and will thus have a random sequence composition. Consequently, the nucleotide sequences flanking the constant DNA sequence will be totally random in a large mixture of restriction fragments.

The present invention therefore also provides specific PCR primers which comprise a constant nucleotide sequence part and in the embodiment of the invention relying to the amplification of a restricted subset of the restriction fragments obtained, a variable sequence part. In the constant sequence part the nucleotide sequence is designed so that the primer will perfectly base pair with the constant DNA sequence of one of the DNA strands at the and of the restriction fragment. The variable sequence part comprises a randomly chosen nucleotide sequence ranging from 1 to 10 bases chosen.

The expression "Variable sequence" more exactly designates a sequence consisting of selected nucleotides forming a sequence which will then remain constant for the purpose of amplifying a subset of restriction fragments. In a particular embodiment of the invention, several sequences of selected bases can be used, in order to define several distinguished primers. In such a case, primers can have the same constant sequence and variable sequences made of selected bases which are different among the primers thus formed.

It is the addition of these variable (selected) sequences to the '3 end of the primers which will direct the preselection of tagged restriction fragments which will be amplified in the PCR step: when the PCR reaction is performed under appropriate conditions the primers will only initiate DNA synthesis on those tagged restriction fragments in which the variable DNA sequence can perfectly base pair with the template strand of the tagged restriction fragment, as illustrated in FIG. 3.

The selection is determined by the number of nucleotides residing in the variable sequence part of the primer: the selectivity of the primers increases with the number of nucleotides in the variable (selected) sequence part. We will also use the term selective bases to denote the nucleotides in the variable sequence part thus showing that the selection of these bases renders the primer selective. It must be realized that a tagged restriction fragment will only be amplified when the selective bases or the primers used recognize both complementary sequences at the ends of the fragment. When the primer matches with only one end, the amplification will be linear rather than exponential, and the product will remain undetected.

It is possible to estimate beforehand the degree of selectivity obtained with variable sequences with different numbers of selective bases, using the general formula $4^{2n}$, where n equals the number of selective bases: using 1 selective base, 1 out of 16 tagged fragments will be amplified, using 2 selective bases, 1 out of 256, using 3 selective bases, 1 out of 4,096, using 4 selective bases, 1 out of 65,536, and so on, will be amplified. One preferred embodiment of the present invention thus allows one to selectively amplify a random subset of tagged restriction fragments from any genomic DNA digest regardless of the number of fragments produced by the restriction enzyme used.

In a preferred embodiment, the number of selective nucleotides is chosen so that the number of restriction fragments which will be amplified is limited to 5 to 200. Although this number can be calculated by dividing the number of fragments by $4^{2n}$, a precise prediction is not possible because not all restriction fragments can be amplified with equal efficiency. Hence, in practice, one finds less fragments of the amplification than theoretically expected. It should also be pointed out that mixtures of two (or more) primers can be used. This will allow the amplification of the fragments recognized by each primer and in addition, the fragments recognized by the two primers. Finally, it should be pointed out that the selection based on the base pairing between the selective nucleotides of the primer and the complementary template is strongly influenced by the temperature chosen for the annealing step in the PCR reaction when this temperature is below or too close to the melting temperature of the primer/template complex, primers will anneal the imperfectly matching template sequences allowing a mismatch to occur in the complex. This should be avoided because it will lead to the amplification of many more fragments than predicted, producing more variable results.

The PCR products obtained in accordance with the invention can be identified tubing standard fractionation methods for separating DNA molecules according to size followed by staining of the DNA molecules with appropriate agents. Alternatively, the primers used for the PCR amplification can be tagged with a staining radio-active labelled or fluorescent chromophore thus allowing the identification of the reaction products after size fractionation. In a preferred embodiment of the invention the PCR products are fractionated by gel electrophoresis using standard gel matrices such as, but not limited to, agarose, polyacrylamide or mixed agarose/polyacrylamide. The PCR products obtained according to the invention will be denoted further by the term Amplified Restriction fragments (ARF).

The means and method of the present invention can be used to generate sets of ARF from restriction digests of any complex genome. The invention permits the number of restriction fragments obtained to be tuned in accordance with the resolution of the gel fractionation system used to separate the ARFs. In one particular embodiment the selective primers are designed to produce 5 to 10 ARFs which are then separated by agarose gel electrophoresis. Another particular embodiment involves the use of selective primers which are designed to produce 20 to 50 ARFS which are then separated on a high resolution gel electrophoresis system such as, but not limited to, polyacrylamide gels or mixed polyacrylamide-agarose gels.

In one preferred embodiment, the restriction enzyme or enzymes are chosen to yield restriction fragments in the size range of 20 to 1000 base pairs, because as is generally known for PCR amplification, this fragment size range is amplified most effectively. Although much fragments can be fractionated on various standard gel matrices, best results are obtained by fractionation on denaturating polyacrylamide gel systems as are currently used for DNA sequencing.

Figure 9:
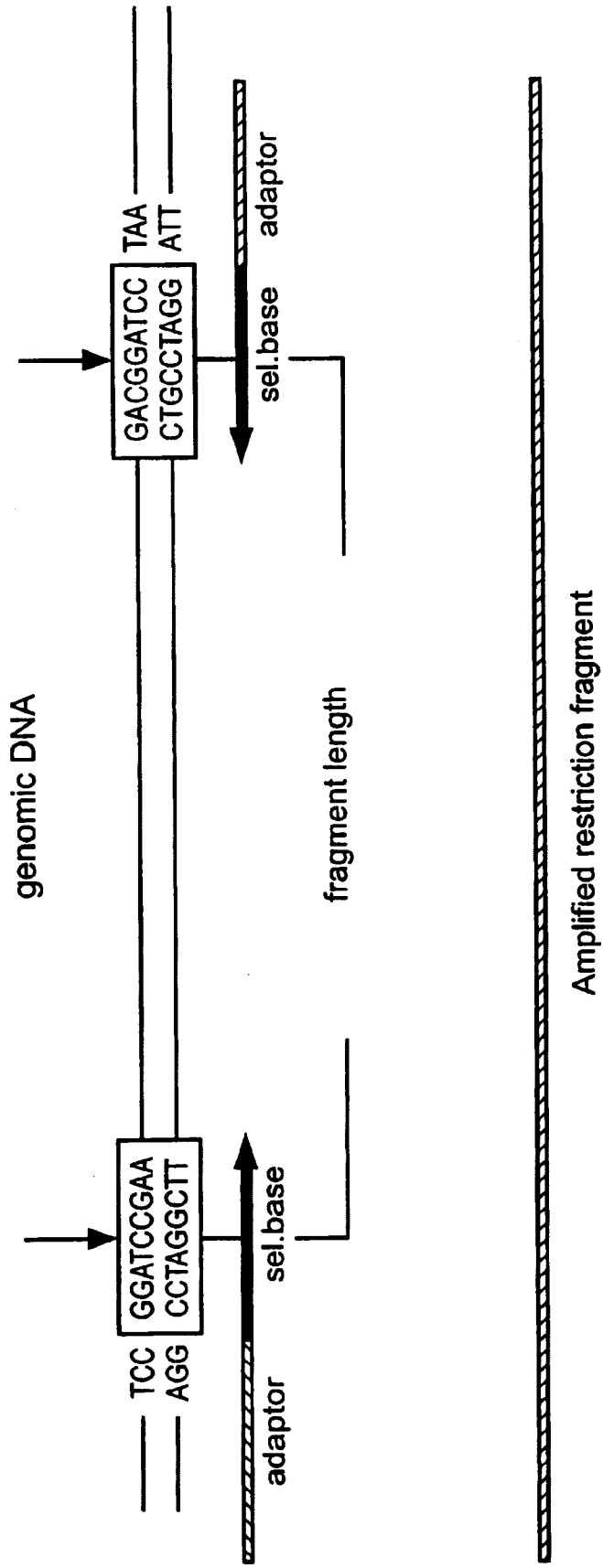
FIG. 9 (SEQ ID NO:90) depicts the general sequence elements which are recognized with the method of selective restriction fragment amplification, including the two nucleotide sequences which are recognized and the distance separating the two sequences.

In accordance with the invention, different sets or ARFS are obtained with each different selective primer in the PCR amplification reaction. The patterns of ARFS identified after separation constitute unique and perfectly reproducible fingerprints of the genomic DNA. Such fingerprints can have several applications such as, but not limited to, forensic typing, the diagnostic identification of organisms, and the identification of species, races, varieties or individuals. The level of identification will be determined by the degree of similarity (the degree of variability) exhibited by different members of a specific group. The variability or similarity is determined by the degree of variation in the nucleotide composition of the related genomes. The underlying principle of the invention is that in each Amplified Restriction fragment two nucleotide sequences are detected which are separated from each other by a given distance, as is illustrated in FIG. 9. Each of the two nucleotide sequences is composed of two parts: (a) the target site for the restriction endonuclease and (b) the nucleotide sequence adjacent to the target site which is included in the selective primer. In related organisms, species, varieties, races or individuals these sequence elements and their relative distances will be conserved to a greater or lesser degree. Hence, the fingerprints constitute a basis for determining the degree of sequence relationships between genomes. On the other hand, difference in the ARF patterns can be used to distinguish genomes from each other. The particular advantages of the present invention over other methods for fingerprinting genomes is the high resolution that can be obtained with the method: several tens or even hundreds of ARFs can be compared simultaneously.

Figure 10:
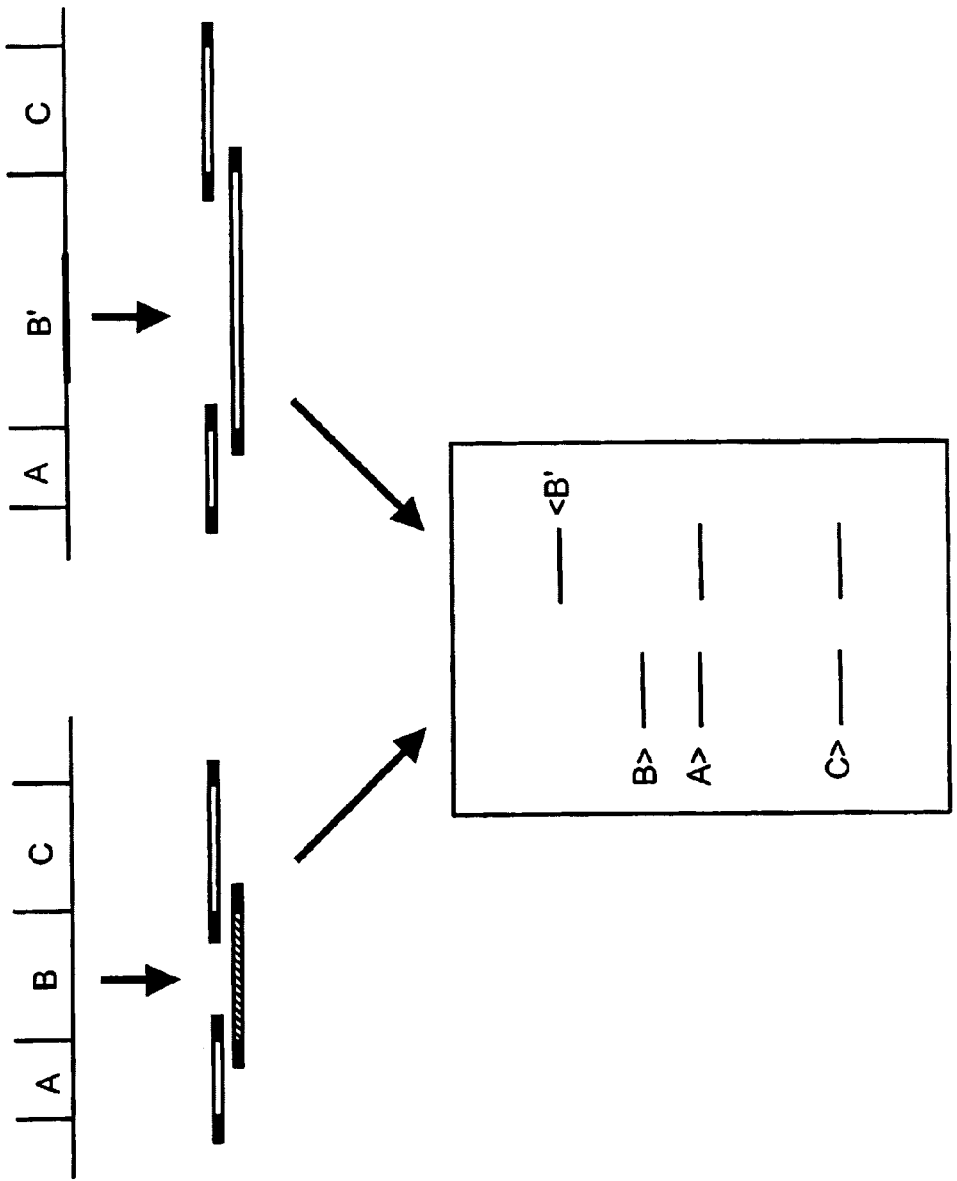
FIG. 10 depicts the types of nucleotide sequence variations which are detected in the method of identifying amplified fragment length polymorphisms.

Another particular application of the present invention involves the screening and identification of restriction fragment polymorphisms (RFP). Changes in the nucleotide composition of genomic DNA often result in polymorphisms of restriction fragments: insertions or deletions affect the size of the restriction fragments containing them (FIG. 10), nucleotide changes can result in the elimination of restriction endonuclease target sites or the creation of new restriction endonuclease target sites. The most commonly used techniques for identifying such changes are Southern blotting experiments using cloned DNA probes, a technique usually referred to as restriction fragment length polymorphism, (RFLP) detection. This technique , involves the extensive screening of randomly cloned DNA fragments in Southern blotting experiments for associated RFLPs among different genomes. In accordance with the method of the present invention, RFPs can be identified directly by comparing the ARFs obtained from different genomes. In principle, the method of the present invention is more sensitive for detecting RFPs because not only differences in the target sites of the restriction endonuclease are detected, but also differences in the adjacent nucleotide sequences comprised to the selective PCR primers. Consequently, the method of the present invention constitutes a far superior method for detecting RFPS.

RFLPs are now currently used for several applications including forensic typing, monitoring of genetically inherited diseases in humans and monitoring the inheritance of agronomic traits in plant and animal breeding. The underlying principle is that certain DNA polymorphism which are closely linked with specific genetic traits can be used to monitor the presence or absence of specific genetic traits.

According to the method of the present invention, the analysis of ARF patterns can be used to define the genetic linkage of polymorphic ARFs with specific genetic traits. Such polymorphic ARFs will be further referred to as Amplified Fragment Length polymorphisms (AFLPs) to distinguish them from RFLP type DNA polymorphisms detected in Southern blotting experiments using cloned DNA probes.

One particular application of the present invention involves the detection of AFLPs linked to specific genetic traits. The application involves the analysis of ARF patterns obtained with different selective primers in restriction digests of genomic DNA of closely related individuals exhibiting differences in the specific genetic trait and the use of analysis techniques that can find correlations between the inheritance of one or more AFLPs and the phenotype exhibited by the specific genetic traits.

Figure 8:
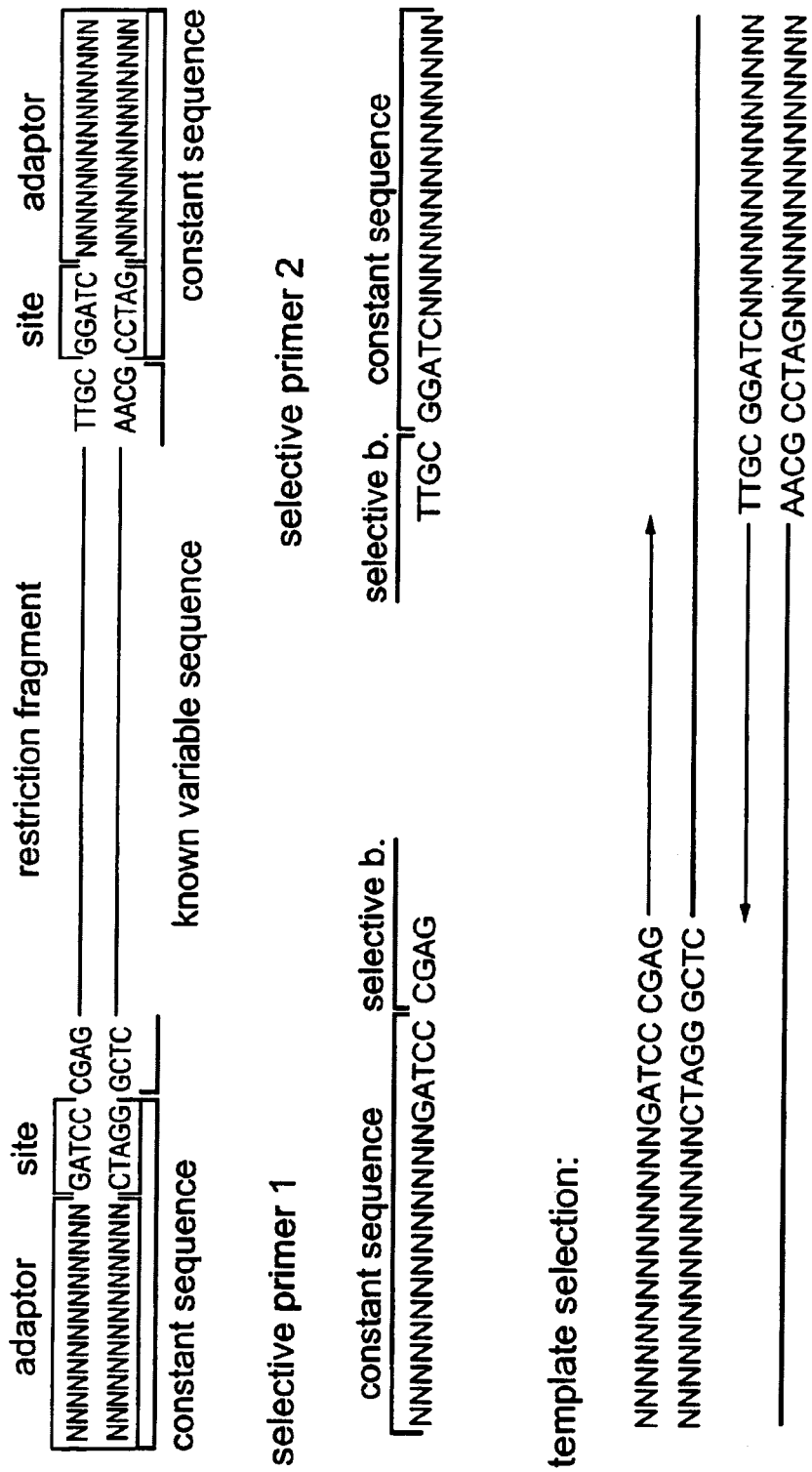
FIG. 8 (SEQ ID NO:84–89) shows the principle of fragment specific amplification using a combination of two PCR primers each comprising 4 selective bases. Each primer forms a double-stranded structure in the different strand of the restriction fragment and thereby forms a primer/template complex from which DNA synthesis can be initiated (represented by the arrows).

A second preferred embodiment of the present invention involves the use of the method of the invention to identify one or more specific restriction fragments. One specific restriction fragment can be amplified from a complex mixture of tagged restriction fragments by first determining the nucleotide sequence of the first 8–12 bases at each end of the restriction fragment. Based on these sequences one can design two primers with each 5 to 10 selective nucleotides exhibiting a sequence complementary to that of the sequence flanking the restriction site or the complementary strand of the restriction fragment. Using such sets of primers one can obtain, after PCR amplification, a single amplified fragment. The restriction fragment used in this method can be either a cloned restriction fragment or an amplified restriction fragment. Since not many restriction fragments cannot be amplified very efficiently, the preferred method of the invention for identifying polymorphic DNA markers involves first amplifying randomly chosen set of fragments and identifying AFLPs which yield strong bands after PCR amplification. These AFLPs can be characterized by sequencing to develop restriction fragment specific primers. Typically, the AFLPs will be isolated by cutting out the corresponding DNA band from the gel, and determining the nucleotide sequences at both ends to establish the sequence of the first 5 to 10 nucleotides adjacent to the restriction endonuclease target sites. Once these nucleotide sequences are known, restriction fragment specific primers can be designed which will only amplify a single restriction fragment from a genomic DNA digest. In this particular embodiment of the invention, one set of two different, selective primers can be used for detecting a specific restriction fragment. In each of the two selective primers or one set the selective bases are chosen such that they are complementary to the nucleotide sequence adjacent to the restriction endonuclease target site, as is illustrated in FIG. 8. The number of selective bases to be included in each primer depends upon the complexity of the restriction endonuclease fragment mixture.

The PCR technique has developed tremendously over the past few years and is rapidly becoming one of the most widely used diagnostic methods in human health care. Its application includes amongst others detection of infectious diseases and detection of genetically inherited diseases. Each diagnostic test is based on the use of two specific synthetic oligonucleotides which are used as primers in the PCR reaction to obtain one or more DNA fragments of specific lengths. In disease detection the test will detect the presence of as little as one DNA molecule per sample, giving the characteristic DNA fragment. In the case of genetically inherited diseases the primers are designed such that their products can discriminate between normal and disease alleles. The distinction either relies on sequence differences in the DNA segment in the genome which is complementary to the primer or, on distance differences between the two primers.

Because the primers exhibit an extremely high degree of specificity, it is possible to monitor different diseases simultaneously, a method often referred to as multiplex PCR. The multiplex PCR method, however, suffers from the limitation that generally only few, 5 to 8, different traits can be monitored simultaneously. The scientific basis for this limitation is that the optimal conditions for PCR amplification (annealing temperature, Mg+ concentration, primer concentration) vary considerably depending on the pair of primers used. In multiplex PCR compromise conditions have to be established under which all primer pairs yield detectable products. In addition, superimposed upon this phenomenon there is the phenomenon of strong differences in the efficiency of amplification or different fragments. Consequently, one often has encountered the problem that products of certain primer pairs are not detectable in multiplex PCR reactions.

The methods of the present invention in essence overcomes these limitations of multiplex PCR, because all the primers used in the present invention have a substantial part of their nucleotide sequence in common. Furthermore, by selecting AFLPs, we select DNA markers that are amplified with equal efficiency. Hence, the optima of the PCR amplification conditions for the different selective primers exhibit much less variation than is observed with commonly used sequence specific primers. In essence, ideal compromise between the number or bases in the synthetic oligonucleotide which are necessary to obtain the required specificity of detecting a single DNA fragment of a given size in a complex genome, which is calculated above, and the length and composition of the oligonucleotide which is optimal for efficient PCR amplification. The method of the invention thus provides a far superior method for multiplex PCR.

The present invention provides a general method for isolating DNA markers from any genome and for using such DNA markers in all possible applications of DNA fingerprinting.

The following examples and figures provide an illustration of the invention which is nevertheless not limited to these examples.

EXAMPLES

Example 1

Selective Restriction Fragment Amplification of Tomato DNA Using PstI

A) Isolation and modification of the DNA

Total Tomato DNA (*Lycopersicon esculentum* c.v. Moneymaker) was isolated from young leaves as described by Bornatzski and Tanksley (Theor. Appl. Genet. 72, 314–321). The typical yield was 50–100 µg DNA per gram of fresh leaf material. The DNA was restricted with PstI (Pharmacia) and double-stranded (ds) PstI-adapters were ligated to the restriction fragments following the procedure described below. These adapters had the following structures (SEQ ID NO:1–2)

```
5- CTCCTAGACTGCGTACATGCA -3

3-     CATCTGACGCATGT      -5
```

The 3'TGCA-overhang in these adapters anneals to the staggered ends created by PstI. The PstI recognition sequence CTGCAG is not restored upon ligation of the adapter, because the 5' C-residue is replaced by A. The ligation reaction was designed in such a way that the end result is almost exclusively DNA fragment-to-adaptor molecules. This was achieved by: 1. Using non-phosphorylated adapters, which excludes adapter-to-adapter ligation, 2. Performing the ligation and restriction reaction at the same time. The latter procedure results in restriction of any fragment-to-fragment ligation product thereby eliminating these products almost completely. Adapter-to-fragment ligation products cannot be restricted by the restriction enzyme, because the PstI recognition sequence is not restored in these products. The reaction conditions used for the adapter ligation were:

2 µg Tomato DNA
0.2 mg adapters
20 units PstI
1 unit T4 DNA-ligase
10 mM Tris.HAC pH 7.5, 10 mM MgAc, 50 mM KAc,
2 mM dithiotreitol, 0.5 mM ATP The ligation reaction was performed in a reaction volume of 20 µl for 3 hours at 37° C. After the adapter ligation, non-ligated adapters were removed by selective precipitation. For this purpose the reaction mixture was increased to 100 µl and NH4AC was added to a final concentration of 2.5 M. 100 µl ethanol of −20° C. was added and the mixture was incubated for 5 minutes at room temperature. The DNA was collected by centrifugation for 14 minutes at 14000 rpm in a cooled eppendorf centrifuge at 4° C. The DNA pellet was washed once with 0.5 ml or 70% ethanol at room temperature, and dissolved in 40 µl of T0.1E (10 mM Tris.HCl pH 8.0, 0.1 mM EDTA). The DNA was stored at −20° C. The selective precipitation procedure described here removes the non-ligated adapters efficiently from the reaction mixture, but small DNA-fragments (≦200 bp) are also lost.

B) The amplification reaction

The DNA prepared above was used as template for amplification of the PstI-fragments. The reaction mixture for the PCR contained:

1 ng template DNA
150 ng primer
1 unit Taq DNA polymerase (Perkin Elmer)
200 µM of all 4 dNTP's
10 mM Tris.HCl pH 8.5, 1.5 mM MgCl2, 50 mM KCl
H2O to a total volume of 50 µl The reaction mixture was covered with 20 µl of light mineral oil to prevent evaporation during the amplification reaction. The PCR was performed on a Perkin Elmer DNA Thermal Cycler using the following cycle profile: 1 minute at 94° C., 1 minute at 60° C., a temperature increase from 60° C. to 72° C. at a rate of 1° C./5 seconds, and 2½ minute at 72° C. A total of 33 cycles were performed. After the reaction 20 µl chloroform was added, and 10 µl of loading dye, in this case 50% sucrose with 0.1% w/v of the dye Orange G, (Merck). This was then :mixed well with the reaction mixture and briefly centrifuged to separate the organic fase (mineral oil and chloroform) from the reaction mixture supplemented with the loading dye. 20 µl of this reaction mixture was analysed on a 1.0% agarose gel.

C) Amplification of Tomato DNA with primers of increasing selectivity

Tomato DNA restricted with PstI and tagged with the PstI-adapter was amplified using the conditions specified above. Four different primers were selected with the sequence: (SEQ ID NO:3–6)

1.  5-CTCGTAGACTGCGTACA-3

2.     5-GACTGCGTACAtgcagA-3

3.     5-GACTGCGTACAtgcagAC-3

4.     5-GACTGCGTACAtgcagACC-3

Figure 11:
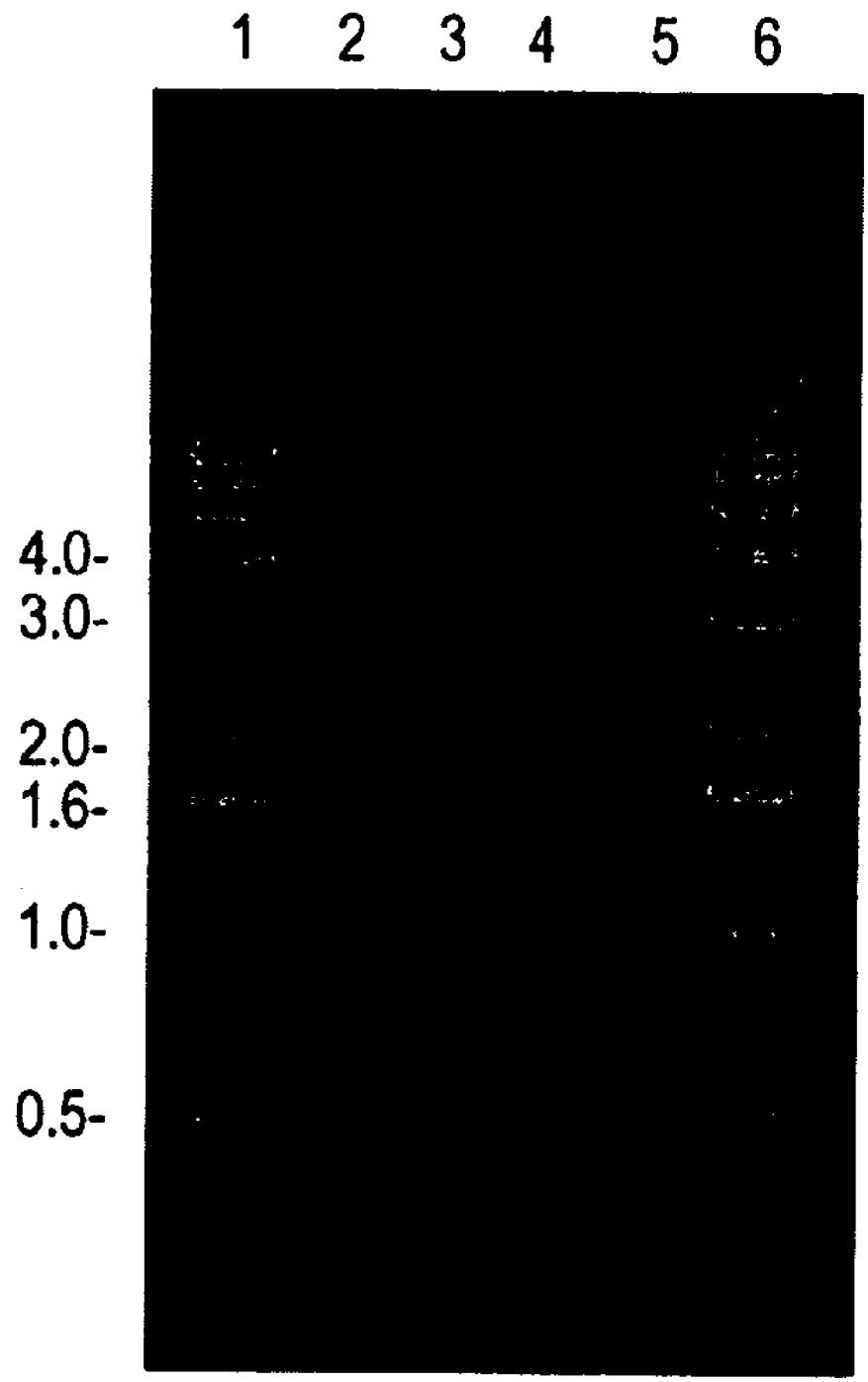
FIG. 11 shows a 1.0% agarose gel with the analysis of the results of the amplification of Tomato DNA restricted with PstI, using primers of increasing selectivity.

Primer 1 is part of the top strand of the adapter used to modify the DNA, and therefore should amplify all PstI-fragments. Primer 2 contains part of the adapter sequence, the PstI-recognition sequence (lower case letters) and one selective nucleotide (bold) and should amplify theoretically about ¹⁄₁₆ part of all PstI-fragments. Primers 3 and 4 are similar to primer 2, but contain 2 and 3 selective nucleotides respectively, and therefore are expected to amplify about ¹⁄₂₅₆ and ¹⁄₁₀₉₆ of the PstI-fragments. Part of the reaction mixtures were analysed on a 1.0% agarose gel, which is shown in FIG. 11. Lanes 1 and 6 of this figure contain DNA markers, of which the sizes are indicated at the left. Lanes 2, 3, 4 and 5 contain the PCR's obtained with primers 1, 2, 3 and 4 respectively. The results indicate that only in case of the primer with 3 selective nucleotides, the number of amplified fragments was such that a clear band pattern was obtained. The other 3 primers gave band patterns, which could not be resolved on agarose gels, because to many PCR products were generated. Within these many PCR products always some fragments predominate, and are seen as bands on a background smear of the other PCR products. Probably these stronger products are present in higher copy numbers on the Tomato genome, or amplify more efficient than the other products. It was anticipated that primers with 3 selective nucleotides had to be used to generate a clear band pattern on agarose gels, because of the total number of PstI-fragments of Tomato genomic DNA (20.000 to 100,000).

D) Analysis of amplified fragments on Southern blots

The amplified fragments were tested on Southern blots to verify that these fragments corresponded to bona fide restriction fragments of the same size. For this purpose four individual fragments obtained with primer 4, were cut out of the agarose gel. The DNA was purified from these gel slices by means of absorption to glass beads (Gene Clean, manufacturer Bio 101), and part of the purified DNA was reamplified to obtain about 1 µg of each of the four DNA fragments. The reamplification reactions were subsequently electrophoresed on a 1.0% preparative agarose gel, and the desired DNA fragments were purified. 200 ng of each fragment was labeled with ($\alpha$-32P)dATP using a random hexamer labelling kit according to procedures advised by the manufacturer (Boehringer Mannheim). Total Tomato DNA was restricted with PstI, and electrophoresed on a 1.0% agarose gel. Four clearly separated lanes each containing about 3 µg or restricted DNA were used. Next, the agarose gel was blotted to a Genescreen+ hybridization membrane as indicated by the manufacturer (New England Nuclear). After blotting the gel was cut in four slices, each containing one lane of the Tomato DNA restricted with PstI. These four slices were each hybridised to one of the four DNA probes following the procedure described by Klien-Lankhorst et al. (Theor. Apll. Genet. 81, 661–667). The hybridised blots were autoradiographed for 40 hours using Kodak XAR5 films. The results obtained showed that all genomic DNA fragments recognised by the four DNA probes, had the same length as these probes. This demonstrated that the amplified fragments, used as probes, originated from the fragments detected on the blots.

E) selective amplification of a single restriction fragment

Three sets of primers were designed for 3 corresponding random PstI-fragments from Tomato genomic DNA, of which the sequence next to the PstI-recognition sequence was known. Sets of primers with 5 selective nucleotides were made as shown below.

Primer set 1:

Sequence 1:(SEQ ID NO:7)

```
           5-ctgcagCAGTACCACC-----CCGGCACCTGctgcag-3

5-TGCGTAACATtgcagCAGTA-3        3-TGGACgacgtACATGCGT-5
```

Primer 1.1(SEQ ID NO:8) Primer 1.2(SEQ ID NO:9)

Primer set 2:

Sequence 2:(SEQ ID NO:10)

```
           5-ctgcagCCGAATCTCT-----AGTGAGTTAGctgcag-3

5-TGCGTACAtgcagCCGAA-3          3-CAATCgacgtACATGCGT-5
```

Primer 2.1(SEQ ID NO:11)
Primer 2.2(SEQ ID NO:12)

Primer set 3:

Sequence 1:(SEQ ID NO:13)

```
           5-ctgcagAATACCAAGA-----GCAACCACAGctgcag-3

5-TCCCTACAtgcagTTATG-3          3-GTGTCgacgtACATGCGT-5
```

Primer 3.1(SEQ ID NO:14) Primer 3.2(SEQ ID NO:15)

Figure 12:
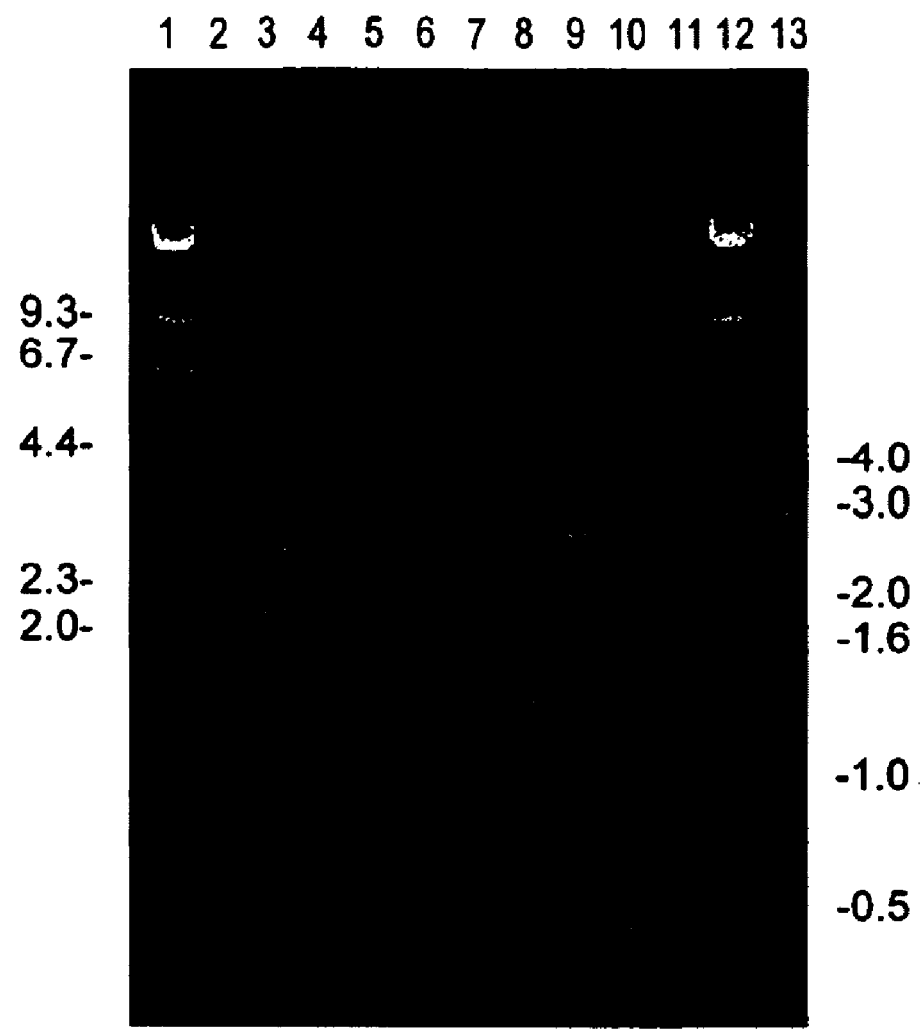
FIG. 12 shows a 1.0% agarose gel with the analysis of the results of specific amplification of 3 different PstI fragment of Tomato DNA using fragment specific primers.

Tomato DNA was digested with PstI and adapters were ligated to the ends or the restriction fragments as described above. This DNA was used as template in PCR's with Primer sets 1 or 2 of 3, using the conditions as described in one of the previous sections. The reaction products of each PCR were analysed on a 1.0% agarose gel. This gel is shown in FIG. 12. FIG. 12 shows 13 lanes, of which lanes 1, 2, 12 and 13 are DNA markers. The sizes in Kilobases of these markers are indicated at both sides of the gel. Lanes 3, 6 and 9 show plasmid DNA with each of the three PstI-fragments restricted with PstI, which yields the vector fragment, pUC10 (Yanisch-Parron et al. Gene 33, 103–119), and the inserted. PstI-fragment. Lanes 4 and 5 show amplification with primer set 1 of 5 fg of the corresponding plasmid DNA and 1 ng of total genomic DNA respectively. Lanes 7 and a show amplification with primer set 2 of plasmid DNA and total genomic DNA, and lance 10 and 11 show amplification with primer set 3. These results demonstrate that it is possible to amplify a single PstI-fragments out of a mixture of at least 20,000 fragments using the selective restriction fragment amplification technique with primers having 5 selective nucleotides.

F) Identification of DNA polymorphisms using SRFA

In the previous sections it was clearly demonstrated that with the selective restriction fragment amplification technique it is possible to amplify restriction fragments, either at random, or specific fragments, when sequence information in available. Hence, it should by possible to search for restriction site polymorphisms between two individuals of the same species. This is described below for two Tomato lines, which are very related but differ in the presence of the root knot nematode resistance gene, Mi, in one of the lines. This Mi-gene originates from *Lycopersicon peruvianum*, a species distantly related to the edible Tomato *L. esculentum*. It has been introduced into the *L. esculentum* line by crossing, and subsequent back crossing 12 times to the *L. esculentum* parent, and selecting the offspring for presence of the Mi-gene. Therefore, the two Tomato lines differ only in a small portion of their genetic material, i.e. the Mi-gene and surrounding region. The Mi-region was calculated to constitute <1% of the genome of this line, using classical genetic methods.

Figure 13:
FIG. 13 shows a 2.5% polyacrylamide/1% agarose gel with DNA fingerprints obtained by Selective Restriction Fragment Amplification (SRFA) of two Tomato lines.

DNA was isolated from the two Tomato lines (line 83M-71392, Mi-sensitive, and line 83M-71398, Mi-resistant, obtained from De Ruiter Seeds, Bleiswijk, The Netherlands) and subsequently restricted with PstI and provided with adapters as described above. A large number of amplification reactions were performed using primers, which differed in their extension of selective nucleotides. Three selective nucleotides were used, and apart form single primers also combinations of two different primers ware used. The reactions were analysed on mixed polyacrylamide/agarose gels: 2.5% polyacrylamide and 1.0% agarose was used, with a ratio acrylamide to bisacrylamide of 20:1. Gels were run on a Protean II gel unit (biorad), using spacers of 1.5 mm. A total of 16 different primers was used giving to reactions with a single primer, and 120 reactions with all possible combinations of two primers. A typical example of a gel with six of these combinations is shown in FIG. 13. Lanes 1 and 14 of this gel contain DNA markers, of which the sizes in kilobases are indicated at the right side of the gel. Lances 2 and 3, 4 and 5, 6 and 7 etc. contain amplifications with a specific primer or primer pair of the two Tomato lines. The screening for restriction site polymorphisms yielded a number a fragments, three of which were very prominent and which are depicted in lanes 9, 11 and 12 of FIG. 13 (indicated by a small circle). The polymorphic bands in lanes 9 and 11 were expected to be the same, because the same primer was present in both reactions (the difference is the presence of a second primer in lane 11). The two polymorphic fragments of lanes 31 and 12 were cut out of the gel, the gel slices were crushed by forcing them through a 18 gauge needle and the DNA was eluted from the gel slices by elution through diffusion in 200 µl of 100 mM Tris.HCl pH 8.0, 10 mM EDTA. 2 µl was used for reamplification or these fragments as described above. 200 ng of each fragment was made blunt end using T4 DNA polymerase and subsequently ligated to 100 ng of plasmid vector pUC18 (Yanisch-Perrun et al., Gene 33, 103–119) restricted with SmaI. The ligation mixture was transformed to *E. coli* and for each fragment one recombinant *E. coli* clone was selected for sequence analysis. All these manipulations were performed using standard procedures as described by Sambrock, Fritsch and Maniatis in: Molecular Cloning, A Laboratory Manual (Cold Spring Harbor Laboratory Press, New York).

Two sets of primers with G selective nucleotides were synthesised based on the sequences of the two fragments as described above. We were able to amplify each fragment specifically using these primer sets. Fragments were only amplified from the Tomato line, from which they originated. Hence, these primer gels exhibited the same polymorphism, initially found with the primers with 3 selective nucleotides used to find this polymorphism.

Example 2

Selective Restriction Fragment Amplification of Tomato DNA with Two Restriction Enzymes In example 1 the principle of selective restriction fragment amplification (SRDA) is exemplified using Tomato DNA and the restriction enzyme PstI. In this example SRFA using two different restriction enzymes, PstI and MseI, will be illustrated.

Isolation and modification of the DNA

Total Tomato DNA was isolated from young leaves as described in example 1. Two pairs of so called isogenic lines were used as source of the DNA, named $Gem^R$ and $Gem^s$, and GCR26 and CCR151 respectively (These lines are described in the following references: Denby and Williams, [1962], Can. J., Plant Sci. 42, 601–685, Smith and Ritchie, [1983], Plant Mol. Biol. Rep. 1, 41–45). The two individuals of each pair of isogenic lines are genetically very similar, but differ in the presence of a trait conferring resistance to the fungal pathogen *Verticillium albo-stratum*.

The first step of the modification of the DNAs comprised the restriction of the DNAs with the two enzymes PstI and MseI. The restriction of the DNA, and also the subsequent ligation of the adapters to the DNA-fragments was carried out in the same buffer, which was named RL-buffer (restriction-ligation buffer), and which contained: 10 mM Tris.HAC/ 10 mM MyAc/50 mM KAc/5 mM DTT, pll 7.5.

Restriction of the DNAs with PstI and MseI 2.5 µg DNA
   12.5 units PstI (Pharmacia, 10 units/µl)
   12.5 units MseI (N.E. Biolabs, 4 units/µl)
   5 µl 10×RL-buffer
   H2O to 50 µl
   Incubation was carried out at 37° C. for 1 hr.

The next step in the modification of the DNAs was the ligation of adapter molecular to the ends of the DNA fragments. First appropriate double-stranded adapter molecules had to be prepared.

Preparation of adapters

```
MseI-adapter:  (SEQ ID NOS: 16-17)  5-GACGATGAGTCCTGAG-3
                                    3-TACTCAGGACTCAT-5
```

For preparation of a solution of 50 pMoles/µl or this adapter 8 µg (1430 pMoles) or the 16-mer 5-GACGATGAGTCCT-GAG-3 was mixed with 7 µg (1430 pMoles) of the 14-mer 5-TACTCAGGACTCAT-3 in a total volume of 28.6 µl or H2O.

```
PstI-adapter: (SEQ ID NOS: 18-19) 5-bio-CTCGTAGACTCCGTACATGCA-3
                                  3-CATCTGACGCATGT-5
```

For preparation of a solution of 5 pMoles/µl of this adapter 5.25 µg (715 pMoles) of the biotinylated 21-mer 5-bio-CTCGTAGACTGCCTACATGCA-3 was mixed With 3.5 µg (715 pMoles) of the 14-mer 5-TCTACCCACTCTAC-3 in a total volume of 143 µl of H2O.

Ligation of the adapter molecules

To the restricted DNA a mix of 10 µl was added containing:

1 µl PstI bio-adapter (=5 pMol)
   1 µl MseI adapter (=50 pMol)
   1.2 µl 10 mM ATP 1 pl 10×RL-buffer
   1 unit T4 DNA ligase (Pharmacia, 5 units/µl)
   H2O to 10 µl The resulting reaction mix of 60 µl was incubated for 3 hours at 37° C.

The adapters were designed in such a way that the restriction sites were not restored after ligation. In this way fragment-to-fragment ligation was prevented, since fragment concatamers are restricted, because the restriction enzymes were still active during the ligation reaction. Adapter-to-adapter ligation was possible because the adapters were not phosphorylated (see also example 1).

Selection of biotinylated DNA-fragments

Preparation of the template-DNAs for SRFA using two restriction enzyme generally involved an extra step not used when using SRFA with a single enzyme. In this step the DNA-fragments to which a biotinylated adapter was ligated were separated from all other fragments.

Biotinylated fragments were separated from non-biotinylated fragments (MseI-MseI-fragments) in this step, by binding to paramagnetic streptavidine beads (Dynal). 10 µl beads were washed once in 100 µl STEX (100 m NaCl/10 mM Tris.HCl/1 mM EDTA/0.1% Triton X-100 pH 8.0), and resuspended in 140 µl STEX. The beads were subsequently added to the ligation mixture, to give a final volume of 200 ml. This was incubated for 30 minutes with gentle agitation at room temperature, to ensure proper binding of the biotinylated DNA-fragments to the beads. The beads were collected by holding the tubes containing the beads close to a magnet. This prevented the beads from being pipetted when the supernatant was transferred to another tube. The beads were washed once, and subsequently transferred to a fresh tube. Then the beads were washed 3 times with 200 µl STEX. Finally the beads were resuspended in 200 µl T01.E The DNAs restricted with the restriction enzymes, provided with adapters, attached to the paramagnetic streptavidine beads and purified from the MseI-MseI fragments prepared as described above will be referred to as template-DNAs in the following steps.

Amplification of PstI-MseI fragments

The template-DNAs prepared as described above should contain all PstI-MseI fragments from the mentioned Tomato lines, and in addition a small amount of PstI-PstI-fragments with no internal MseI-fragments. In this experiment a number of these PstI-MseI fragments were visualised by amplification, essentially as described in example 1. Gel analyses of the amplification products was performed on denaturing acrylamide gels (Maxam and Gilbert, Proc. Natl. Acad. Sci. U.S.A. 74, 560–564), because the kind of fragments obtained by the procedure described in this example were much smaller than the ones described in example 1. In addition these types of gels allowed the separation of up to 100 bands per lane, which was about ten times more than the agarose gels described in example 1. The fragments were visualised by labeling one of the PCR-primers at the 5' end with $(r-^{32}P)ATP$ and polynucleotide kinase.

Labeling of the PCR-primer

The primer selected for labeling was the 19-mer (SEQ ID NO:20) 5-GATGAGTCCTGAGTAAgaa-3 which was named MseI-primer-1, and in which the selective nucleotides are indicated with lower case letters. The labeling was performed in the following way:

3.0 µl 18-mer (from solution of 50 ng/µl=150 ng)

5.0 µl $(r-^{32}P)$-ATP (from solution of 10 µCi/µl=50 µC*i*)

3.0 µl 250 mM Tris.HCl/100 mM MgCl$_2$/50 mM DTT, pH 7.5

0.5 µl T4-kinase (Pharmacia 10 units/µl)

18.5 µl H2O

This gave a total volume of 30 µl, which was incubated at 37° C. for 30 minutes. For each PCR 1 µl of this 5'labeled primer was added.

A total of 28 PCRs were performed, in which each of the 4 template-DNAs were amplified with 7 primer combinations. Each primer combination had the same MseI-primer (MseI-primer-1, described above), but varied in the choice of the PstI-primer. A total of 7 different primers were chosen (As with the MseI-primer the selective nucleotides are indicated with lower case letters):

```
PstI-primer-1: (SEQ ID NO: 21) 5-CACTCCCTACATGCAGga-3
PstI-primer-2: (SEQ ID NO: 22) 5-GACTGCGTACATGCAGgt-3
PstI-primer-3: (SEQ ID NO: 23) 5-GACTGCGTACATGCAGgg-3
PstI-primer-4: (SEQ ID NO: 24) 5-GACTGCGTACATGCAGag-3
PstI-primer-5: (SEQ ID NO: 25) 5-GACTGCGTACATGCAGat-3
PstI-primer-6: (SEQ ID NO: 26) 5-GACTGCGTACATGCAGct-3
PstI-primer-7: (SEQ ID NO: 27) 5-GACTGCGTACATGCAGta-3
```

(10 mM Tris/0.1 mM EDTA, pH 8.0), and transferred to a fresh tube. The DNA was kept at 4° C.

All PCR-primers were dissolved in H2O at a concentration of 50 ng/µl.

21

The amplification reaction

The PCR-mixture consisted of:

2.0 μl of template-DNA 1.0 μl of 5'labeled MseI-primer (5 ng)

0.5 μl unlabeled MseI-primer (25 ng)

0.6 μl PstI-primer (30 ng)

2.0 μl of 100 mM Tris.HCl/15 mM $MgCl_2$/500 mM KCl, pH 8.5

0.8 μl of 5 mM dNTPs 0.1 pl of Taq polymerise (Cetus Perkin Elmer, 5 units/μl)

13.0 μl of H2O

All components of the reaction were added and mixed well, an essential component of the PCR, generally the enzyme, was added last. Subsequently the reaction was started as soon as possible.

The amplifications were performed on a Perkin Elmer 9600 thermal cycler. The cycle profile was as follows:

| 1 cycle: | denaturation: | 30 sec at 94° C. |
|---|---|---|
| | annealing: | 30 sec at 65° C. |
| | extension: | 60 sec at 72° C. |
| 11 cycles: | denaturation: | 30 sec at 94° C. |
| lower annealingtemperature 0.7° C. each cycle, | | |
| 64.3° C., 63.6° C., 62.9° C., 62.2° C., 61.5° C., | | |
| 60.8° C., 60.1° C., 59.4° C., 58.7° C., 58.0° C., | | |
| 57.3° C. Incubate for 30 seconds at each temperature. | | |
| extension: 60 sec at 72° C. | | |
| 23 cycles: | denaturation: | 30 sec at 94° C. |
| | annealing: | 30 sec at 56° C. |
| | extension: | 60 sec at 72° C. |

Gel analysis of amplified fragments

The reaction products were analyzed on 4.5% denaturing polyacrylamide gels. 50×38 cm gels were used, of which the gel cassettes to prepare these gels were purchased from Biorad. 100 ml of gel solution was used containing 4.5% w/v acrylamide/0.225% w/v bisacrylamide/7.5 M Urea/50 mM Tris/50 mM Boric acid/1 mM EDTA, pH 8.3. 100 ml gel solution was mixed with 500 μl 10% Ammonium persulfate and 100 μl TEMED immediately before casting the gel. A Tris/Boric acid/EDTA-buffer was used as electrophoresis buffer and contained: 100 mM Trie/100 mM Boric acid/2 mM EDTA, pH 8.3. The reaction mixtures were mixed with an equal volume (20 μl) of 98% formamide/10 mM EDTA/0.01% w/v bromo phenol blue/0.01% w/v Xylene cyanol. The resulting mixtures were heated for 3 minutes at 95° C., and then quickly cooled on ice. 2 μl of each sample was loaded on the gel. Gels were run at constant power of 110 watts to give a constant heat development during electrophoresis. Under these conditions the field strength of the gels corresponded to 40 to 50 Volt/cm.

Figure 14:
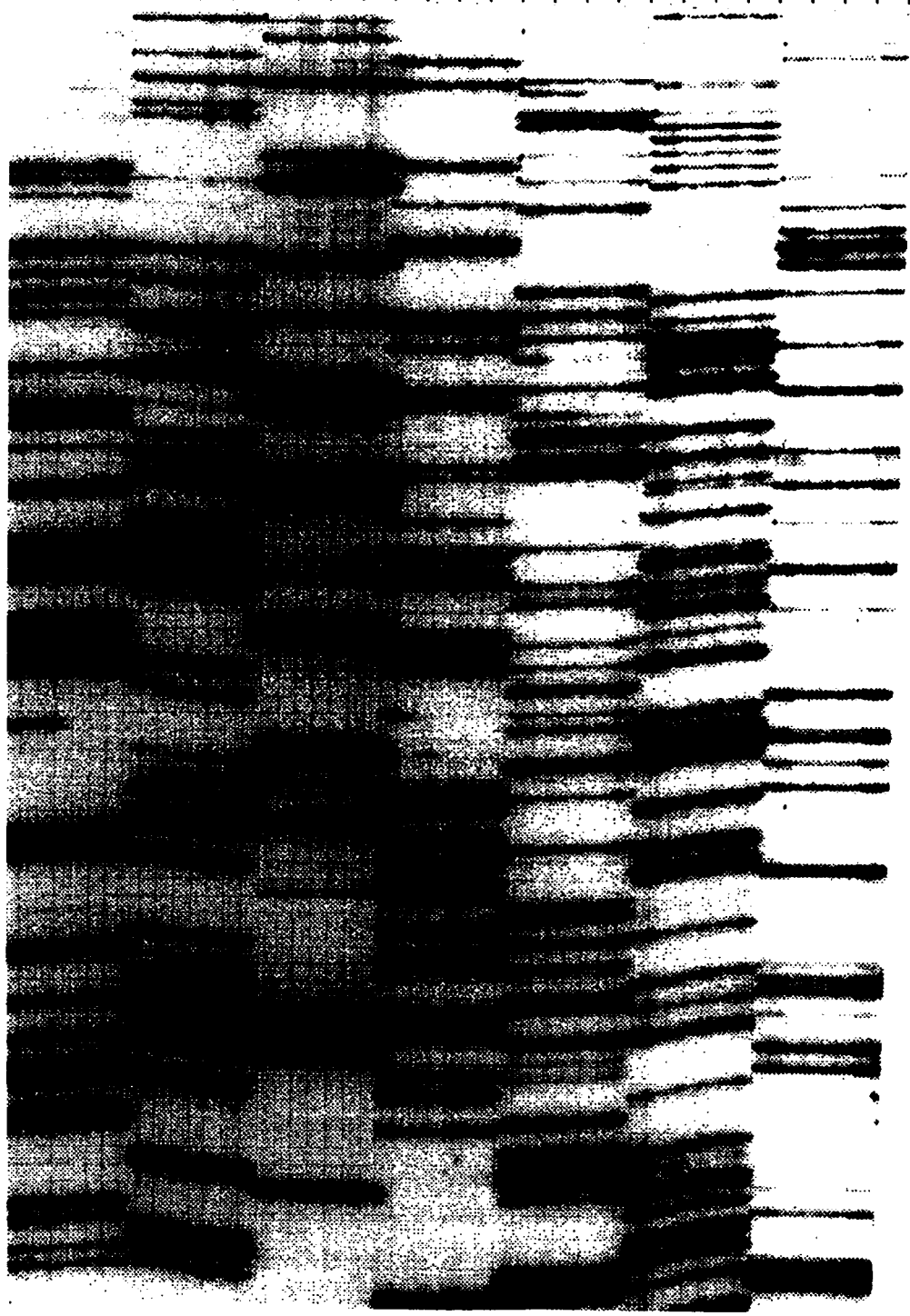
FIG. 14 shows part of a 4.5% denaturing polyacrylamide gel with DNA fingerprints of 4 Tomato lines using SRFA with the enzyme combination PstI/MseI.

The results of the SRFA reactions are shown in FIG. 14. The lanes are numbered from 1 to 28, and contain each time the four Tomato lines with one of the 7 primer combinations. The order of the Tomato lines on the gel is: 1. GCR26, 2, GCR151, 3. $Gem^R$, 4. $Gem^S$. Lanes 1 to 4 contain these DNAs amplified with MseI-primer-1 and PstI-primer-1, lanes 5 to 8 contain these DNAs amplified with MseI-primer-1 and PstI-primer-2, lanes 9 to 12 contain these DNAs amplified with MseI-primer-1 and PstI-primer-3, lanes 13 to 16 contain these DNAs amplified with MseI-primer-1 and PstI-primer-4, lanes 17 to 20 contain these DNAs amplified with MseI-primer-1 and PstI-primer-5, lanes 21 to 24 contain these DNAs amplified with MseI-primer-1 and PstI-primer-6, and lanes 25 to 28 contain these DNAs amplified with MseI-primer-1 and PstI-primer-7. The gel contains no size markers but the DNA fragments visualised correspond with 200 nucleotides at the bottom of the Figure to ±500 nucleotides at the top.

Example 3

Selective Restriction Fragment Amplification of DNA of Various Lactuca Species with Two Restriction Enzymes In example 2 the principle of selective restriction fragment (SRFA) amplification using two restriction enzymes is exemplified for Tomato DNA. In this example we will illustrate that similar results are obtained using DNAs of various Lactuca species using the same two restriction enzymes PstI and MseI.

Isolation and modification of the DNA

DNAs were isolated as described in example 1 using young leaf material of various Lactuca species. As indicated below these plants include a commercial lettuce (*L. sativa*) variety, and several individuals of two wild *Lactuca* species, *L. saligna* and *L. virosa*. The plants were arbitrarily designated the following names:

1, *L. saligna*, nr. 21, plant 1
2, *L. saligna*, nr. 21, plant 2
3, *L. saligna*, nr. 22, plant 1
4, *L. saligna*, nr. 22, plant 2
5, *L. virosa*, nr. 01, plant 1
6, *L. virose*, nr. 01, plant 2
7, *L. virosa*, nr. 02,
8, *L. virosa*, nr. 03, plant 1
9, *L. virosa*, nr. 03, plant 2
10. *L. sativa*, a commercial butterhead variety The genetic material analysed thus represented 6 different plant types, including two different individuals of 1 of these plants.

Modification of the Lactuca DNA3 to generate the templates for the SRFA was performed identical to the procedure described in example 2.

Amplification of PstI-MseI fragments

The DNAs prepared as described above were used as templates for SRFA reactions. Two primer combinations were used employing a single MseI-primer and two different PstI-primers. These primers (selective nucleotides depicted in lower case letters) were:

```
MseI-primer:    (SEQ ID NO: 28)    5-GATGAGTCCTCAGTAAaca-3

PstI-primer-1:  (SEQ ID NO: 29)    5-GACTGCGTACATGCAGaa-3
```

```
PstI-primer-2: (SEQ ID NO: 30)     5-GACTGCGTACATGCAGca-3
```

Figure 15:
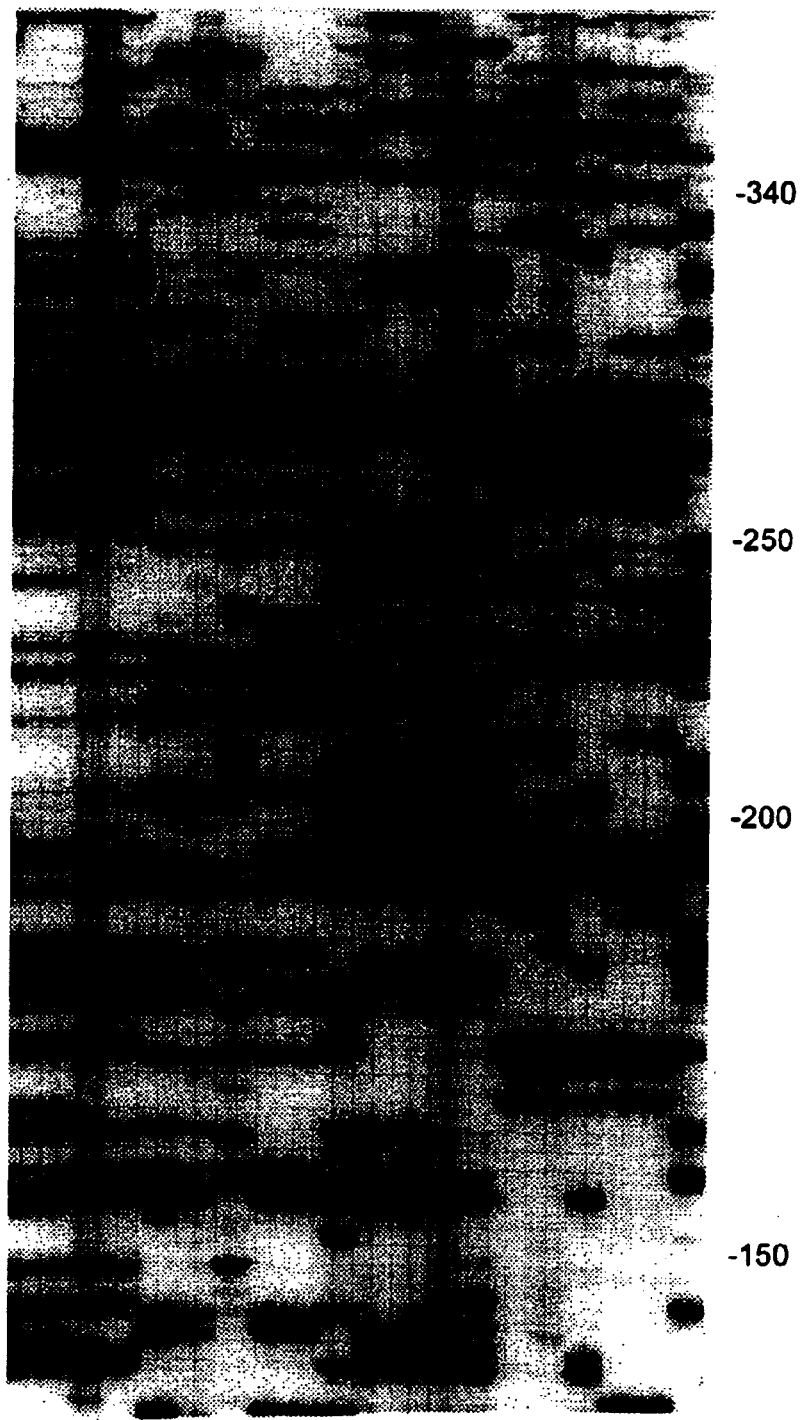
FIG. 15 shows part of a 4.5% denaturing polyacrylamide gel with DNA fingerprints of 10 Lactuca lines using SRFA with the enzyme combination PstI/MseI.

Amplification of PstI-MseI fragments using the primers depicted above was carried out exactly as described in example 2, and the generated fragments were visualised on denaturing polyacrylamide gels as described in example 2. The band patterns obtained are shown in FIG. 15. Lanes 1 to 10 show DNAs 1 to 10 amplified with the MseI-primer in combination with PstI-primer-1, lanes 11 to 20 show DNAs 1 to 10 amplified with the MseI-primer in combination with the PstI-primer 2. Size markers (not visible in this Figure) in nucleotides are indicated to the right of the gel. The differences in band patterns reflects the differences in relatedness of the various plants.

Example 4

Selective Restriction Fragment Amplification of Corn Inbred Lines with a Variety of Restriction Enzyme Combinations In example 2 and 3 the principle of selective restriction fragment (SRFA) amplification using two restriction enzyme is exemplified using Tomato DNA and Lettuce (*Lactuca* species) DNAs respectively. In this example it will be illustrated that similar results are obtained with Corn (*Zea mais*) lines. In addition it will be illustrated that a variety of restriction enzyme combinations can be used to obtain DNA fingerprints of in this case Corn lines.

Isolation and modification of the DNA

Two corn inbred lines were used, named 1 and 2. The source of these lines is irrelevant, because in our experience any selected line gave good DNA fingerprints using SRFA. DNA of these lines was isolated from young leaf material as described by Saghai-Mahoof et al. (1984), Proc. Natl. Acad. Sci. U.S.A. 81, 8014–8018). The following restriction enzyme combination (EKs) were used to make the template-DNAs: PstI/TaqI, EcoRI/TaqI, AseI/TaqI, Sse8387-T/TaqI All enzymes were purchased from Pharmacia, except As I which was purchased from New England Biolabs, and Sse8387-I which was purchased from Amersham. Template DNAs were prepared essentially as described in examples 2 and 3, with the following exceptions:

Restriction of the DNA was performed by first incubating with TaqI at 65° C. for one hour, and subsequently incubating with the second enzyme, PstI, AseI, EcoRI or Sse8387-I, for an additional hour at 37° C. Ligation of adapters was as described in example 2 using the following adapters:

```
TaqI-adapter: (SEQ ID NOS: 31–32) 5-GACGATGAGTCCTGAC-3
                                  3-TACTCACCACTGGC-5

PstI & Sec8387-I-adapter: (SEQ ID NOS: 33–34) 5-bio-CTCGTAGACTGCGTACATGCA-3
                                              3-CATCTGACGCATGT-5

AseI-adapter: (SEQ ID NOS: 35–36) 5-bio-CTCGTAGACTGCGTACC-3
                                  3-CTCACGCATGGAT-5

EcoRI-adapter: (SEQ ID NOS: 37–38) 5-bio-CTCGTAGACTGCGTACC-3
                                   3-CTGACGATGGTTAA-5
```

Amplification of restriction fragments

Amplification of restriction fragments was performed as described in example 2. The primers selected for labeling of the amplification products were the following TsqI-primers having 3 selective nucleotides (indicated by lower case letters):

```
TaqI-primers: (SEQ ID NOS: 39–42)   1. 5-TGAGTCCTGACCGAacc-3
(5' labeled)                        2. 5-TGAGTCCTGACCGAaca-3
                                    3. 5-TGAGTCCTGACCCAcaa-3
                                    4. 5-TGAGTCCTGACCGAcac-3
```

These 4 primers were used for detection of amplification products with all four enzyme combinations. For each mega combination 4 primers for the other enzyme were selected to give a total of 16 combinations for each enzyme. These primers are indicated below (selective nucleotides shown in lower case letters). For EcoRI and AseI primers with 3 selective nucleotides were selected, for PstI primers with 2 selective nucleotide were chosen, and for SseI primers with a single selected nucleotide were chosen. For enzymes cutting less frequently in the Corn genomic DNA, primers were selected containing extensions with fewer selective nucleotides

```
EcoRI-primers: (SEQ ID NOS: 43–46)   1. 5-CTGCGTTACCAATTCcaa-3
                                     2. 5-CTGCGTTACCAATTCaca-3
                                     3. 5-CTGCGTTACCAATTCaac-3
                                     4. 5-CTGCGTTACCAATTCcag-3
```

```
AseI-primer: (SEQ ID NOS: 47–50)    1. 5-GACTGCGTACCTAATaa-3
                                    2. 5-GACTGCGTACCTAATaag-3
                                    3. 5-CACTGCGTACCTAATacc-3
                                    4. 5-GACTGCGTACCTAATgaa-3

PstI-primers: (SEQ ID NOS: 51–54)   1. 5-GACTGCGTACATGCAGac-3
                                    2. 5-CACTGCGTACATGCAGaa-3
                                    3. 5-GACTGCGTACATGCAGca-3
                                    4. 5-GACTGCGTACATCCACcc-3

Sse8387-I-primers: (SEQ ID NOS: 55–58) 1. 5-CACTGCGTACATGCAGGa-3
                                       2. 5-GACTGCGTACATGCAGGg-3
                                       3. 5-GACTGCGTACATCCACCc-3
                                       4. 5-GACTGCGTACATGCAGGt-3
```

Figure 16:
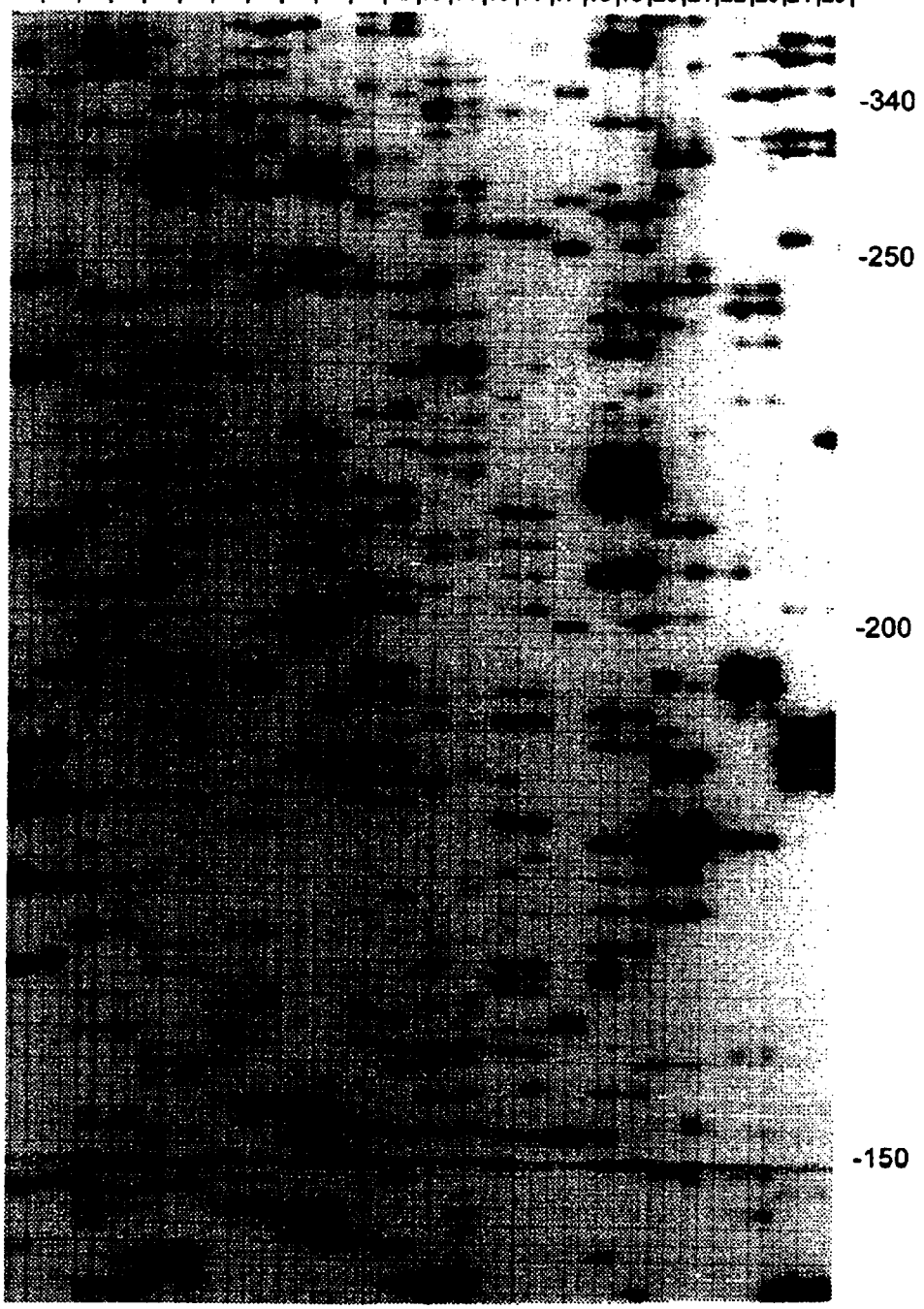
FIG. 16 shows part of a 4.5% denaturing polyacrylamide gel with DNA fingerprints of 2 Corn lines using SRFA with the enzyme combinations PstI/TaqI and EcoRI/TaqI.

A total of 128 PCRs were performed (2 DNAs×4 enzyme combinations×16 primer combinations), following the protocol described in example 2. The reaction products of these PCBs were analysed on 3 gels (containing 48 lanes/gel) as described in example 2. All primer combination gave DNA fingerprints of 50 to 100 bands per lane, except for the combination SecI TaqI, which gave only 10 to 15 bands per lane. An example of one of the gels is shown in FIG. 16. This Figure shows part of the gel with the analysis or DNA fingerprints obtained with the enzyme combinations PstI/TaqI and EcoRI TaqI. Lanes 1 to 8 show DNA-fingerprints of the two corn DNAs obtained by SRFA with TaqI-primer-3 and PetI-primers-1, -2, -3 and -4 respectively, lanes 9 to 16 show DNA-fingerprints of the two Corn DNAs obtained by SRFA with TaqI-primer-4 and PetI-primers-1, -2, -3 and -4 respectively, lane 17 shows the size marker lambda-DNA restricted with PstI, of which the sizes of some of the fragments in nucleotides are indicated at the right, and lanes 18 to 25 show DNA-fingerprints of the two Corn DNAs obtained by SRFA with TaqI-primer-1 and EcoRI-primers-1, -2, -3 and -4 respectively.

Example 5

Selective Restriction Fragment of Bacterial DNAs

In example 2, 3 and 4 the principle of selective restriction fragment (SRFA) amplification using two restriction enzymes is exemplified for Tomato, Lettuce (*Lactuca* species) and Corn DNAs respectively. In this example it will be illustrated that this technique can also be used to characterise bacterial DNAs. A number of *Xanthomonas campestris* strains were obtained from the Laboratory of Microbiology in Ccnt, Belgium, to illustrate the usability of the technique in bacteria, isolation and modification of the DNA All DNAs were prepared from *Xanthomonas campestris* strains isolated from a variety or origins, mostly from infected plants. These strains, numbered 1 to 26 are listed below, end may be obtained from the Laboratory of Microbiology in Ghent, Belgium.

| DNA | subspecies | pathovar | isolate |
|---|---|---|---|
| 1. | albilineans | | 494 |
| 2. | fragariae | | 708 |
| 3. | oryzae | oryzae | 5047 |
| 4. | oryzae | populi | 5743 |
| 5. | maltophilia | | 958 |
| 6. | campestris | campestris | 568 |
| 7. | campestris | alfalfae | 497 |
| 8. | campestris | coracanae | 686 |
| 9. | campestris | citri | 8655 |
| 10. | campestris | citri | 9658 |
| 11. | campestris | citri | 9181 |
| 12. | campestris | citri | 8657 |
| 13. | campestris | citri | 8654 |
| 14. | campestris | citri | 8650 |
| 15. | campestris | citri | 682 |
| 16. | campestris | citri | 681 |
| 17. | campestris | citri | 9325 |
| 18. | campestris | citri | 9321 |
| 19. | campestris | citri | 9176 |
| 20. | campestris | citri | 9671 |
| 21. | campestris | citri | 9665 |
| 22. | campestris | citri | 9182 |
| 23. | campestris | citri | 560 |
| 24. | campestris | citri | 9167 |
| 25. | campestris | citri | 9175 |
| 26. | campestris | citri | 9160 |

DNA of these bacterial strains was isolated as described by Marmur (J. Mol. Biol. 3, 208–218). The DNAs were restricted essentially as described in example 4, with the exception that TaqI and ApaI were chosen as restriction enzymes. Ligation of adapters was as described in example 4 using the following adapters:

```
TaqI-adapter: (SEQ ID NOS: 59–60)   5-GACGATGAGTCCTGAC-3
                                    3-TACTCAGGACTGGC-5

ApaI-adapter: (SEQ ID NOS: 61–62)   5-bio-TCGTAGACTGCGTACAGGCC-3
                                          3-CATCTGACGCATGT-5
```

27

Amplification of restriction fragments

Amplification of restriction fragments was performed as described in example 2. The primers selected for SRFA were the TaqI-primer (SEQ ID NO:63) CGATGAGTCCTGAC-CGAg-3 (having one selective nucleotide indicated in lower case letter), and the ApaI-primer 5-GACTGCGTACAGGC-CCg-3 (having use selective nucleotide indicated to lower case letter). The ApaI-primer was labeled at the 5'end for detection of the amplified fragments as described in example 2.

Each of the 26 DNAs was amplified using the primer set described above. Amplification conditions were as described in example 2, except that the last 9 cycles of the PCR were omitted, because of the lower complexity of the DNAs compared to the plant DNA in examples 2, 3 and 4.

Figure 17:
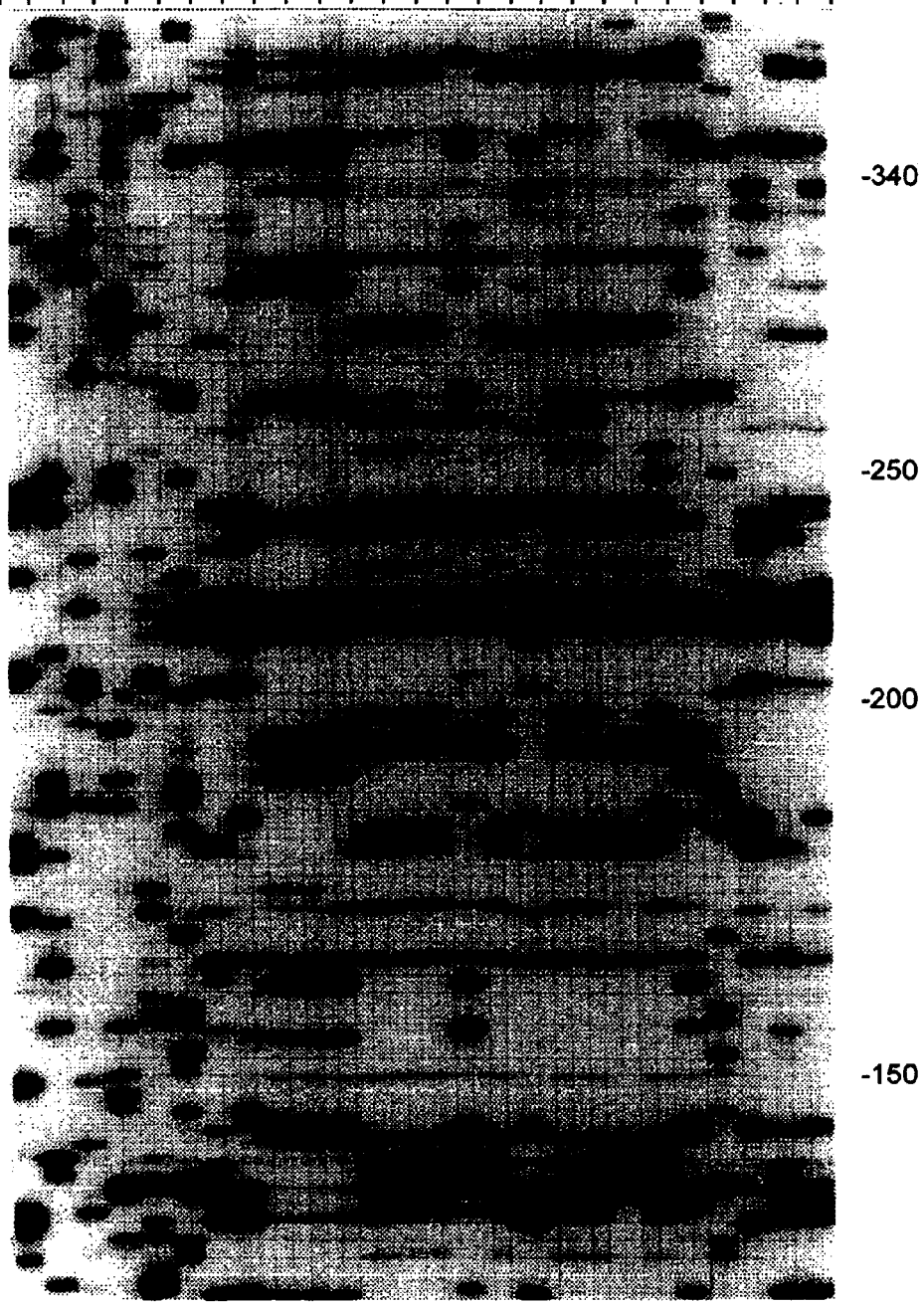
FIG. 17 shows, part of a 4.5% denaturing polyacrylamide gel with DNA fingerprints of 26 *Xanthomonas campestris* strains using SRFA with the enzyme combination ApaI/TaqI.

The DNA fingerprints obtained with the bacterial DNAs as described in this example are shown in FIG. 17. Lanes 1 to 26 represent bacterial DNAs 1 to 26. The sizes of marker DNAs (not visible on the gel) in nucleotides are indicated to the right of the gel. This figures shows clearly that the relatedness of the bacterial strains is reflected by the similarity of the band patterns.

Example 6

Selective Restriction Fragment Amplification of DNA of Various Animals with Two Restriction Enzymes In the previous examples selective restriction fragment amplification (SRFA) was exemplified for plant DNA of various sources. Here we illustrate the efficacy of the procedure using random samples of DNA obtained from different domestic animals. The animal species tested are: *Callus domesticus* (chicken): *Suceerofa domestica L*. (pig); *Boa taurus* (cow); *Equus caballus* (horse). Restriction enzymes used are Sse8387I and MseI.

Isolation and modification of the DNA

DNAs were isolated from blood samples following procedures described by Maniatis et al., (1983). DNA samples 1 to 3 (chicken), 4 to 7 (pig), 8 to 11 (cow) and 12 to 15 (horse) were digested as restriction enzymes Sse8387I and MseI. The DNA fragments were ligated to adapters as described in example 2. Since the restriction enzymes Sse8387I and PstI generate compatible 3'overhangs we could use the PstI- and MseI-adapter described in example 2.

Amplification of restriction fragments

Template DNAs named above and prepared as described in example 2 served as templates in SRFA reactions. The primer combinations used consisted of a single MseI-primer and different SseI-primers:

```
MseI-primer: SEQ ID NO: 65        5-GATGAGTCCTGACTAAtac-3

Sse8387I-primer-1 : SEQ ID NO: 66  5-GACTGCCTACATGCAGGaa-3

Sse8387I-primer-2 : SEQ ID NO: 67  5-GACTGCGTACATGCAGGag-3
```

Figure 18:
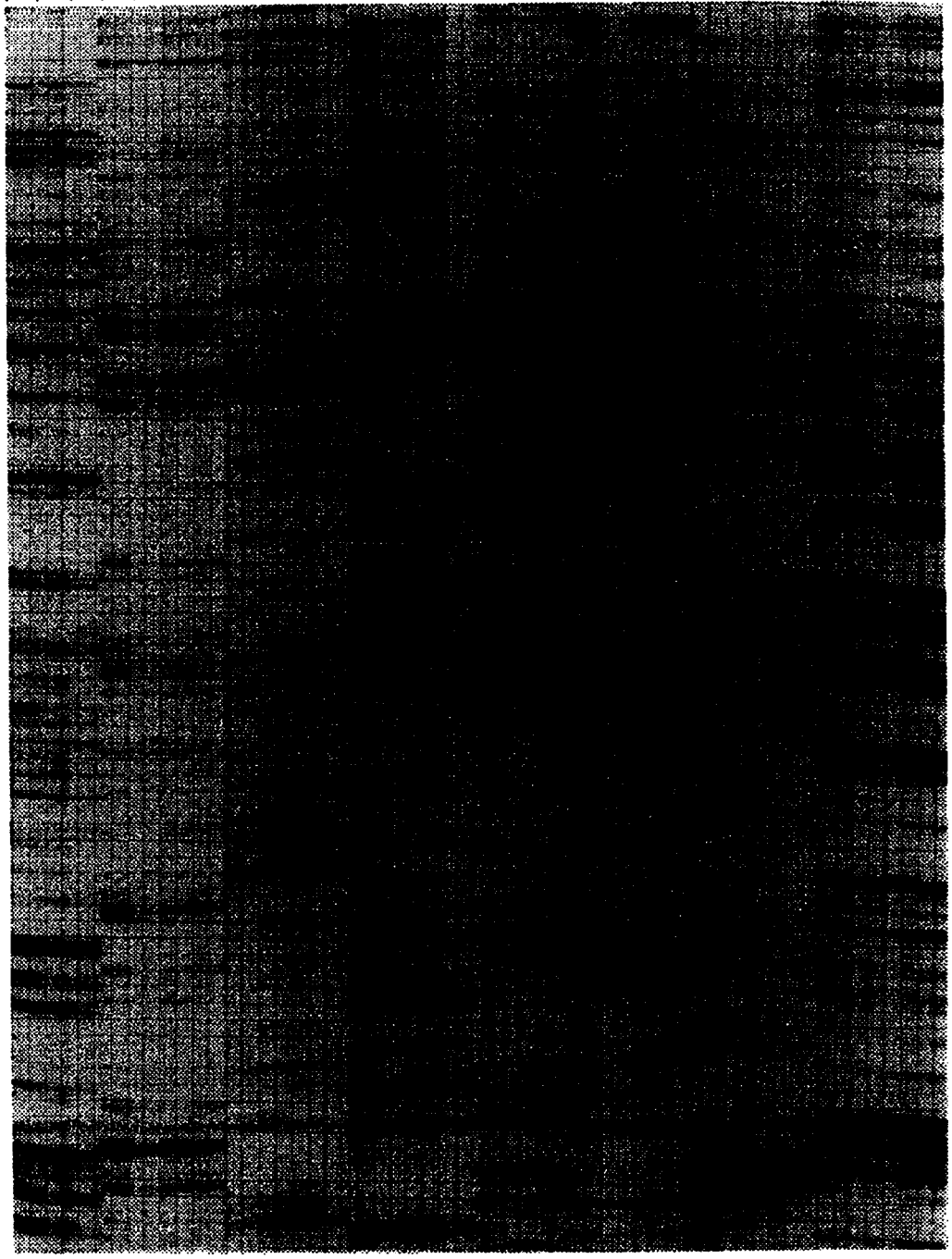
FIG. 18 shows part of a 4.5% denaturing polyacrylamide gel with DNA finger prints of different individuals of d domestic animals Chicken, Pig, Cow and Horse using SRFA with the enzyme combination SseI/MseI.

Amplification of Sse8387I-MseI fragments using primer pairs described above was carried out using the protocol described in example 2. Reaction products were run on denaturing polyacrylamide gels also described in example 2. An autoradiograph showing fingerprints of the above samples is shown in FIG. 18. Lanes 1 through 15 show fingerprints of DNAs 1 to 15 amplified with the MseI-primer paired with Sse8387I-primer-1, lanes 16 through 30 show similar patterns obtained with the MseI-primer combined with Sse83871-Primer-2. Differences in fingerprints between animals of one species reflect heterogeneity in animal populations; overall-patterns are characteristic for a specific species.

In a particular embodiment the invention relates to a process for the controlled amplification of at least one part of a starting DNA which contains a plurality or restriction sites for a determined specific restriction endonuclease, and of which at least part of its nucleic acid sequence is unknown, which process comprises:

(a) digesting said starting DNA with said specific restriction endonuclease to fragment it into the corresponding series of restriction fragments which respectively comprise 5' ends and 3'ends;

(b) unless the 5' and 3' adaptors defined hereafter were already in separate forms, also digesting with said specific endonuclease, a determined double-stranded oligonucleotide linker including itself a single site within its own nucleotidic sequence for said specific endonuclease to thereby cleave said linker in such 5' and 3' adaptors respectively:

(c) ligating the restriction fragments obtained from the starting DNA at their 5' and 3' ends with said 3' and 5' adaptors respectively to thereby produce tagged restriction fragments of the starting DNA, which fragments then comprise at their respective 5' and 3' ends tags whose nucleotide sequences then comprise those of the 3' and 5' adaptors including the nucleotides involved in the specific restriction site;

(d) unless, where appropriate to provide suitable templates for primers, said 5' and 3' adaptors were prior to the preceding ligation prolonged by adding thereto oligonucleotide segments of determined constant sequences at their respective 5' and 3' ends, prolonging, where appropriate for the same purpose, the corresponding ends of said tagged restriction fragments with said oligonucleotide segments, whereby tagged restriction fragments elongated at both ends with said constant sequences are obtained;

(e) contacting said tagged or when appropriate, elongated restriction fragments under hybridizing conditions with two oligonucleotide primers;

(f) wherein said primers include sequences having the same nucleotide sequence as the terminal parts of the strands of the 5' and 3' ends of said tagged or, when appropriate, elongated restriction fragments which are themselves complementary to the strands acting as templates for said primers, said primers respectively including the nucleotides complementary to those involved in the formation of the site for said determined specific restriction endonuclease in the template strand;

(g) amplifying said elongated restriction fragments hybridized with said primers by PCR or similar techniques in the presence of the required nucleotides and polymerase to cause further elongation of the hybridized primers along those restriction fragments of the starting DNA to which said primers initially hybridized on their entire length, and (h) identifying or recovering said last mentioned restriction fragments.

In a particular embodiment of this process, the terminal nucleotide of at least one of said primers in the direction of the elongation sought corresponds to the last of the nucleotides involved in the restriction site for said specific endonuclease, and which process comprises identifying or recovering the restriction fragments of said starting DNA which have been amplified.

In another particular embodiment of this process, at least one of said primers includes a selected sequence comprising a determined number (one or several nucleotides) extending beyond the last of the nucleotides involved in the restriction site for said specific endonuclease in the direction of its own elongation within the corresponding restriction fragments during the amplification step.

In a specific embodiment of the above-described process, double-stranded DNA-linker contains several sites for different specific endonucleases which are all distinct from one another, which processes comprise repeating, on a same starting DNA the steps of the process defined above with one of these restriction endonucleases yet with another of said distinct specific endonucleases and upon using primers whose nucleotide sequences are selected as defined in the above description, yet with respect to said other specific endonuclease.

The process described above or of the oligonucleotide of the invention, is appropriate, for the identification of polymorphisms in determined DNAs originating from the same live species, e.g. genomic DNAs of a microbial, plant or animal, including human, or of fragments thereof, either among themselves or relative to a corresponding determined DNA standard, which use comprises subjecting the DNAs under study to the process or to the contact of the oligonucleotide in conditions allowing an amplification or elongation reaction, comparing the restriction patterns obtained starting from each of said DNAs and, optionally, of said standard DNA and relating the existence and, where appropriate, the localization of that DNA polymorphism to the differences observed between the sizes of the restriction fragments of the different DNAs.

The invention also relates to a fragmented DNA whose different fragments have sequences which all correspond to initial digests of the unfragmented starting DNA from which they are produced with a same determined specific endonuclease, characterized in that all of said fragments were tagged at their 5' and 3' ends respectively as determined 3' and 5' adaptors corresponding to the cleaved part of a same starting DNA linker which initially included a single restriction site for said specific endonuclease, and optionally prolonged with determined constant sequences. The fragmented DNA can be in the form of a pattern of migration bands on a suitable support, e.g. gel support, in which its fragments had Initially been caused to migrate under the influence of an electric field.

The fragmented DNA can also comprise and portions including oligonucleotide characterized by the following composition, starting from the 5' end:

(i) a nucleotide sequence (constant sequence) or at least 10 bases, but not longer than 30 bases, complementary to a determined DNA sequence used as adaptor, immediately followed by:

(ii) a nucleotide sequence complementary to the target site of a specific restriction endonuclease used in step (a), in so far as that nucleotide sequence or part of it, is not comprised in (ii), immediately followed by:

(iii) a nucleotide sequence of at least one nucleotide, but shorter than 10 nucleotides, selected, e.g. which is 1 to 5 nucleotides long.

The invention further relates to a kit for the fragmentation of determined DNAs by at least one specific restriction endonuclease into fragments and analysis of these fragments which comprises:

the specific restriction endonuclease;

a double-stranded DNA oligonucleotide linker including itself a single site within its own nucleotidic sequence for said specific endonuclease to thereby cleave said linker in corresponding 5' and 3' adaptors respectively, wherein said double-stranded DNA linker had a sufficient size to provide 5' and 3' parts which may subsequently provide templates for the PCR primers or this kit;

PCR primers which respectively comprise, on the one hand the same sequences as the strands of the 5' and 3' adaptors complementary to the strands subsequently acting as templates for said primers wherein said primers further include the nucleotides complementary to those which are involved in the formation of the site for said determined specific restriction endonuclease in the template strands;

if appropriate, oligonucleotide segments of determined (constant) sequences for generating sites of sufficient length for hybridization with said primers, for the elongation of the 5' ends of said 5' adaptors or the 3' ends of card 3' adaptors or both, prior to digestion of said linker by said specific restriction endonuclease to produce said 5' and 3' adapters respectively, or alternatively for the elongation of the tagged fragments obtained subsequent to the ligation of said 5' and 3' adaptors to the extremities of the fragments of the starting DNA, optionally a fragmented DNA standard corresponding to the determined DNA subject to a fragmentation study, whereby the fragments of said DNA standard were obtained by digesting it with said specific endonuclease.

A particular embodiment of this kit is such that said oligonucleotide segments for the elongation of both card 5' and 3 µl adapters or 5' and 3' only of the tagged DNA fragments, have identical nucleotide sequences.

In another embodiment, the linker of the kit contains several respective unique sites for specific endonucleases all different from one another, said kit further including primers corresponding to each of the 3' and 5' adaptors formed by cleavage of said linker with said different specific endonucleases respectively, wherein said primers are respectively as defined in claim 8, in respect of the 3' and 5' adaptors which are produced in said linker by cleavage thereof by each of said specific endonucleases.

Also in a particular embodiment the kit can comprise fragmented DNA standards as defined above in respect of the corresponding specific restriction endonucleases, wherein each of said fragmented DNA standards is in respect of each of the determined specific restriction enzymes.

What is claimed is:

1. A kit for the fragmentation of target DNAs by one or more restriction endonucleases into fragments, and for the amplification and analysis of a subset of these fragments, which comprises:

the restriction endonuclease or endonucleases;

at least one double-stranded synthetic oligonucleotide adaptor having one end which can be ligated to one or both ends of the restriction fragments of the target DNA;

at least one primer for the amplification of a subset of the restriction fragments of the target DNA, having 10 to 50 nucleotides and having the following structure:
5'-constant nucleotide sequence complementary to at least part of the adaptor—constant nucleotide sequence complementary to at least part of the restriction site of said restriction endonuclease—selective nucleotide sequence—3' wherein said selective nucleotide sequence consists of one to 10 nucleotide residues, may be random or specific, and allows for the selection of a subset of DNA fragments for amplification from said target.

2. A method for identifying or recovering an amplified or elongated subset of DNA fragments from a target DNA regardless of whether its nucleotide sequence is unknown, which method comprises:

(a) digesting said target DNA with at least one restriction endonuclease to fragment said target DNA into restriction fragments;

(b) ligating to the restriction fragments obtained from the target DNA at least one double-stranded synthetic oligonucleotide adaptor having one end which can be ligated to one or both of the ends of the restriction fragments, to thereby produce tagged restriction fragments of the target DNA;

(c) contacting said tagged restriction fragments under hybridizing conditions with at least one primer, wherein said at least one primer has the following structure
5'-constant nucleotide sequence complementary to at least part of the adaptor constant nucleotide sequence complementary to at least part of the restriction site of said restriction endonuclease—selective nucleotide sequence—3' wherein said selective nucleotide sequence consists of one to 10 nucleotide residues, may be random or specific;

(d) amplifying only tagged restriction fragments which hybridize to the selective sequence of said primers in the presence of the required nucleotides and DNA polymerase or elongating said hybridized primers, wherein said selective sequence selects a subset of DNA fragments from the target DNA for amplification or elongation; and (e) identifying or recovering said amplified or elongated subset of DNA fragments as produced in step (d) as DNA fingerprints.

3. A kit for amplifying a subset of restriction fragments obtained from a target DNA using a restriction endonuclease which cuts the target DNA at a restriction site, wherein said kit comprises at least one primer having 10 to 50 nucleotides and having the following structure:

5'-constant nucleotide sequence complementary to at least part of an adaptor—constant nucleotide sequence complementary to at least part of the restriction site of said restriction endonuclease—selective nucleotide sequence—3' wherein said adaptor is a double-stranded synthetic oligonucleotide having one end which can be ligated to one or both ends of the restriction fragments of the target DNA, and said selective nucleotide sequence consists of one to 10 nucleotide residues, may be random or specific, and wherein upon hybridization to said target DNA, said selective sequence selects a subset of DNA fragments from the target DNA for amplification or elongation.

4. A kit according to claim 3 further comprising at least one double-stranded synthetic oligonucleotide adaptor having one end that can be ligated to one or both of the ends of the restriction fragments of the target DNA.

5. A kit according to claim 4 further comprising restriction endonuclease or endonucleases.

6. The kit of claim 1 wherein said selective nucleotide sequence comprises one to 4 nucleotide residues.

7. The kit of claim 3 wherein said selective nucleotide sequence comprises one to 4 nucleotide residues.

8. A set of reagents for amplifying a subset of restriction fragments obtained from a target DNA using a restriction endonuclease which cuts the target DNA at a restriction site, wherein said set comprises at least one adaptor which ligates to a restriction fragment and at least one primer having 10 to 50 nucleotides, which primer has the following structure;

5'-constant nucleotide sequence complementary to at least part of the adaptor—constant nucleotide sequence complementary to at least part of the restriction site of a restriction endonuclease—selective nucleotide sequence—3' wherein said selective nucleotide sequence consists of one to 10 nucleotide residues, may be random or specific, and wherein upon hybridization to said target DNA, said selective sequence selects a subset of DNA fragments from the target DNA for amplification or elongation, and further wherein said at least one adaptor and said at least one primer are in separate mixtures.

9. A primer set for amplifying a subset of restriction fragments from a target DNA, wherein said primer set comprises at least two primers, wherein said primers have 10 to 50 nucleotides and has have the following structure:

5'-constant nucleotide sequence complementary to at least part of an adaptor—constant nucleotide sequence complementary to at least part of the restriction site of a restriction endonuclease—selective nucleotide sequence—3' wherein said selective nucleotide sequence consists of one to 10 nucleotide residues, may be random or specific, and wherein upon hybridization to said target DNA, said selective sequence selects a subset of DNA fragments from the target DNA for amplification or elongation, and wherein each of the two primers have a different nucleotide sequence, and further wherein said primers are either together in the same mixture or are in separate mixtures.

10. The primer set of claim 9 wherein each of said at least two primers have different selective nucleotide sequences.

11. The primer set of claim 9 wherein each of said at least two primers have different constant nucleotide sequences.

* * * * *

SEQUENCE LISTING (1) GENERAL INFORMATION:

(iii) NUMBER OF SEQUENCES: 90

(2) INFORMATION FOR SEQ ID NO:1:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

CTCCTAGACT GCGTACATGC A                                              21

(2) INFORMATION FOR SEQ ID NO:2:

(i) SEQUENCE CHARACTERISTICS:
       (A) LENGTH: 14 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

CATCTGACGC ATGT                                                      14

(2) INFORMATION FOR SEQ ID NO:3:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

CTCGTAGACT GCGTACA                                                   17

(2) INFORMATION FOR SEQ ID NO:4:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:4:

GACTGCGTAC ATGCAGA                                                   17

(2) INFORMATION FOR SEQ ID NO:5:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:5:

-continued

GACTGCGTAC ATGCAGAC                                                      18

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GACTGCGTAC ATGCAGACC                                                     19

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 16..17
        (D) OTHER INFORMATION: /note= "Gap between nucleotides 16 and
            17."

(xi) SEQUENCE DESCRIPTION: SEQ ID NO:7:

CTGCAGCAGT ACCACCCCGG CACCTGCTGC AG                                      32

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

TGCGTAACAT TGCAGCAGTA                                                    20

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TGGACGACGT ACATGCGT                                                      18

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

```
    (ix) FEATURE:
        (A) NAME/KEY: misc_feature
        (B) LOCATION: 16..17
        (D) OTHER INFORMATION: /note= "Gap between nucleotides 16 and
            17."

(xi) SEQUENCE DESCRIPTION: SEQ ID NO:10:

CTGCAGCCGA ATCTCTAGTG AGTTAGCTGC AG                                          32

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

TGCGTACATG CAGCCGAA                                                          18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CAATCGACGT ACATGCGT                                                          18

(2) INFORMATION FOR SEQ ID NO:13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 16..17
        (D) OTHER INFORMATION: /note= "Gap between nucleotides 16 and
            17."

(xi) SEQUENCE DESCRIPTION: SEQ ID NO:13:

CTGCAGAATA CCAAGAGCAA GCACAGCTGC AG                                          32

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

TCCGTACATG CAGTTATG                                                          18

(2) INFORMATION FOR SEQ ID NO:15:
```

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GTGTCGACGT ACATGCGT                                                  18

(2) INFORMATION FOR SEQ ID NO:16:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GACGATGAGT CCTGAG                                                    16

(2) INFORMATION FOR SEQ ID NO:17:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

TACTCAGGAC TCAT                                                      14

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..21
        (D) OTHER INFORMATION: /note= "Nucleotide 1 is
            biotinylated."

(xi) SEQUENCE DESCRIPTION: SEQ ID NO:18:

CTCGTAGACT GCGTACATGC A                                              21

(2) INFORMATION FOR SEQ ID NO:19:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CATCTGACGC ATGT                                                      14
```

(2) INFORMATION FOR SEQ ID NO:20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GATGAGTCCT GAGTAAGAA                                                19

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GACTGCGTAC ATGCAGGA                                                 18

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GACTGCGTAC ATGCAGGT                                                 18

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GACTGCGTAC ATGCAGGG                                                 18

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GACTGCGTAC ATGCAGAG                                                 18

(2) INFORMATION FOR SEQ ID NO:25:

(i) SEQUENCE CHARACTERISTICS:

(A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GACTGCGTAC ATGCAGAT                                                 18

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

GACTGCGTAC ATGCAGCT                                                 18

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GACTGCGTAC ATGCAGTA                                                 18

(2) INFORMATION FOR SEQ ID NO:28:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

GATGAGTCCT GAGTAAACA                                                19

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

GACTGCGTAC ATGCAGAA                                                 18

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GACTGCGTAC ATGCAGCA                                                    18

(2) INFORMATION FOR SEQ ID NO:31:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:31:

GACGATGAGT CCTGAC                                                      16

(2) INFORMATION FOR SEQ ID NO:32:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:32:

TACTCAGGAC TGGC                                                        14

(2) INFORMATION FOR SEQ ID NO:33:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..21
            (D) OTHER INFORMATION: /note= "Nucleotide 1 is
                biotinylated."

(xi) SEQUENCE DESCRIPTION: SEQ ID NO:33:

CTCGTAGACT GCGTACATGC A                                                21

(2) INFORMATION FOR SEQ ID NO:34:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:34:

CATCTGACGC ATGT                                                        14

(2) INFORMATION FOR SEQ ID NO:35:

(i) SEQUENCE CHARACTERISTICS:
            (A) LENGTH: 17 base pairs
            (B) TYPE: nucleic acid

```
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..17
        (D) OTHER INFORMATION: /note= "Nucleotide 1 is
            biotinylated."

(xi) SEQUENCE DESCRIPTION: SEQ ID NO:35:

CTCGTAGACT GCGTACC                                                    17

(2) INFORMATION FOR SEQ ID NO:36:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

CTGACGCATG GAT                                                        13

(2) INFORMATION FOR SEQ ID NO:37:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..17
        (D) OTHER INFORMATION: /note= "Nucleotide 1 is
            biotinylated."

(xi) SEQUENCE DESCRIPTION: SEQ ID NO:37:

CTCGTAGACT GCGTACC                                                    17

(2) INFORMATION FOR SEQ ID NO:38:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

CTGACGCATG GTTAA                                                      15

(2) INFORMATION FOR SEQ ID NO:39:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:
```

```
TGAGTCCTGA CCGAACC                                              17

(2) INFORMATION FOR SEQ ID NO:40:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

TGAGTCCTGA CCGAACA                                              17

(2) INFORMATION FOR SEQ ID NO:41:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

TGAGTCCTGA CCGACAA                                              17

(2) INFORMATION FOR SEQ ID NO:42:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

TGAGTCCTGA CCGACAC                                              17

(2) INFORMATION FOR SEQ ID NO:43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

CTGCGTTACC AATTCCAA                                             18

(2) INFORMATION FOR SEQ ID NO:44:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

CTGCGTTACC AATTCACA                                             18

(2) INFORMATION FOR SEQ ID NO:45:
```

```
      (i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:45:

CTGCGTTACC AATTCAAC                                                    18

(2) INFORMATION FOR SEQ ID NO:46:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:46:

CTGCGTTACC AATTCCAG                                                    18

(2) INFORMATION FOR SEQ ID NO:47:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:47:

GACTGCGTAC CTAATAAC                                                    18

(2) INFORMATION FOR SEQ ID NO:48:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:48:

GACTGCGTAC CTAATAAG                                                    18

(2) INFORMATION FOR SEQ ID NO:49:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:49:

GACTGCGTAC CTAATACC                                                    18

(2) INFORMATION FOR SEQ ID NO:50:

(i) SEQUENCE CHARACTERISTICS:
          (A) LENGTH: 18 base pairs
          (B) TYPE: nucleic acid
```

(C) STRANDEDNESS: single
            (D) TOPOLOGY: linear (ii) MOLECULE TYPE: DNA (genomic)

(xi) SEQUENCE DESCRIPTION: SEQ ID NO:50:

GACTGCGTAC CTAATGAA                                                      18

(2) INFORMATION FOR SEQ ID NO:51:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:51:

GACTGCGTAC ATGCAGAC                                                      18

(2) INFORMATION FOR SEQ ID NO:52:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:52:

GACTGCGTAC ATGCAGAA                                                      18

(2) INFORMATION FOR SEQ ID NO:53:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:53:

GACTGCGTAC ATGCAGCA                                                      18

(2) INFORMATION FOR SEQ ID NO:54:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:54:

GACTGCGTAC ATGCAGCC                                                      18

(2) INFORMATION FOR SEQ ID NO:55:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:55:

GACTGCGTAC ATGCAGGA                                                        18

(2) INFORMATION FOR SEQ ID NO:56:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

GACTGCGTAC ATGCAGGG                                                        18

(2) INFORMATION FOR SEQ ID NO:57:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

GACTGCGTAC ATGCAGGC                                                        18

(2) INFORMATION FOR SEQ ID NO:58:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

GACTGCGTAC ATGCAGGT                                                        18

(2) INFORMATION FOR SEQ ID NO:59:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

GACGATGAGT CCTGAC                                                          16

(2) INFORMATION FOR SEQ ID NO:60:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

TACTCAGGAC TGGC                                                            14

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..20
        (D) OTHER INFORMATION: /note= "Nucleotide 1 is
            biotinylated."

(xi) SEQUENCE DESCRIPTION: SEQ ID NO:61:

TCGTAGACTG CGTACAGGCC                                                20

(2) INFORMATION FOR SEQ ID NO:62:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

CATCTGACGC ATGT                                                      14

(2) INFORMATION FOR SEQ ID NO:63:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

CGATGAGTCC TGACCGAG                                                  18

(2) INFORMATION FOR SEQ ID NO:64:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

GACTGCGTAC AGGCCCG                                                   17

(2) INFORMATION FOR SEQ ID NO:65:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

```
GATGAGTCCT GACTAATAC                                                    19

(2) INFORMATION FOR SEQ ID NO:66:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

GACTGCGTAC ATGCAGGAA                                                    19

(2) INFORMATION FOR SEQ ID NO:67:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

GACTGCGTAC ATGCAGGAG                                                    19

(2) INFORMATION FOR SEQ ID NO:68:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_feature
        (B) LOCATION: 15..23
        (D) OTHER INFORMATION: /note= "between nucleotides 17 and
            18 is a restriction fragment of unknown sequence."

(xi) SEQUENCE DESCRIPTION: SEQ ID NO:68:

NNNNNNNNNN NNNNGATCGA TCNNNNNNNN NNNNNN                                 36

(2) INFORMATION FOR SEQ ID NO:69:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 15..17
        (D) OTHER INFORMATION: /note= "after nucleotide 17 is a
            restriction fragment of unknown sequence."

(xi) SEQUENCE DESCRIPTION: SEQ ID NO:69:

NNNNNNNNNN NNNNGATC                                                     18

(2) INFORMATION FOR SEQ ID NO:70:

(i) SEQUENCE CHARACTERISTICS:
```

```
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: misc_feature
         (B) LOCATION: 15..23
         (D) OTHER INFORMATION: /note= "between nucleotides 17 and
             18 is a restriction fragment of unknown sequence."

(xi) SEQUENCE DESCRIPTION: SEQ ID NO:70:

NNNNNNNNNN NNNNCTAGCT AGNNNNNNNN NNNNNN                              36

(2) INFORMATION FOR SEQ ID NO:71:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: misc_feature
         (B) LOCATION: 15..23
         (D) OTHER INFORMATION: /note= "between nucleotides 17 and
             18 is a restriction fragment of unknown sequence."

(xi) SEQUENCE DESCRIPTION: SEQ ID NO:71:

NNNNNNNNNN NNNNGATCGA TCNNNNNNNN NNNNNN                              36

(2) INFORMATION FOR SEQ ID NO:72:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: misc_feature
         (B) LOCATION: 1..5
         (D) OTHER INFORMATION: /note= "before nucleotide 1 is a
             restriction fragment of unknown sequence."

(xi) SEQUENCE DESCRIPTION: SEQ ID NO:72:

CTAGNNNNNN NNNNNNNN                                                  18

(2) INFORMATION FOR SEQ ID NO:73:

(i) SEQUENCE CHARACTERISTICS:
        (A) LENGTH: 46 base pairs
        (B) TYPE: nucleic acid
        (C) STRANDEDNESS: double
        (D) TOPOLOGY: linear (ii) MOLECULE TYPE: DNA (genomic)

(ix) FEATURE:
         (A) NAME/KEY: misc_feature
         (B) LOCATION: 20..27
         (D) OTHER INFORMATION: /note= "between nucleotides 23 and
             24 is a restriction fragment of unknown sequence."

(xi) SEQUENCE DESCRIPTION: SEQ ID NO:73:

NNNNNNNNNN NNNNGATCCN NNNNNNNNGGA TCNNNNNNNN NNNNNN                  46
```

(2) INFORMATION FOR SEQ ID NO:74:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..22
        (D) OTHER INFORMATION: /note= "Bases 1-19 are a constant
            sequence and bases 20-22 are selective."

(xi) SEQUENCE DESCRIPTION: SEQ ID NO:74:

NNNNNNNNNN NNNNGATCCN NN                                      22

(2) INFORMATION FOR SEQ ID NO:75:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:75:

NNNNNNNNNN NNNNGATCCG AG                                      22

(2) INFORMATION FOR SEQ ID NO:76:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:76:

NNNNNNNNNN NNNNCTAGGC TCNNNNNNNN NNNNNNNNNN NNNNN              45

(2) INFORMATION FOR SEQ ID NO:77:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:77:

NNNNNNNNNN NNNNGATCCG AG                                      22

(2) INFORMATION FOR SEQ ID NO:78:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:78:

NNNNNNNNNN NNNNCTAGGA AGNNNNNNNN NNNNNNNNNN NNNNN            45

(2) INFORMATION FOR SEQ ID NO:79:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 15..22
        (D) OTHER INFORMATION: /note= "after nucleotide 22 is a
            restriction fragment of unknown sequence."

(xi) SEQUENCE DESCRIPTION: SEQ ID NO:79:

NNNNNNNNNN NNNNGATCCG GA            22

(2) INFORMATION FOR SEQ ID NO:80:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 15..23
        (D) OTHER INFORMATION: /note= "after nucleotide 23 is a
            restriction fragment of unknown sequence."

(xi) SEQUENCE DESCRIPTION: SEQ ID NO:80:

NNNNNNNNNN NNNNCTAGGT TCN            23

(2) INFORMATION FOR SEQ ID NO:81:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 15..23
        (D) OTHER INFORMATION: /note= "after nucleotide 23 is a
            restriction fragment of unknown sequence."

(xi) SEQUENCE DESCRIPTION: SEQ ID NO:81:

NNNNNNNNNN NNNNCTAGGG CCN            23

(2) INFORMATION FOR SEQ ID NO:82:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature (B) LOCATION: 15..23
            (D) OTHER INFORMATION: /note= "after nucleotide 23 is a
                restriction fragment of unknown sequence."

(xi) SEQUENCE DESCRIPTION: SEQ ID NO:82:

NNNNNNNNNN NNNNCTAGGA AGN                                             23

(2) INFORMATION FOR SEQ ID NO:83:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 15..32
        (D) OTHER INFORMATION: /note= "between nucleotides 23 and
            24 is a restriction fragment of unknown sequence."

(xi) SEQUENCE DESCRIPTION: SEQ ID NO:83:

NNNNNNNNNN NNNNCTAGGC CTNNTCCCCT AGNNNNNNNN NNNNNN                    46

(2) INFORMATION FOR SEQ ID NO:84:

(i) SEQUENCE CHARACTERISTICS:
        (A) LENGTH: 46 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_feature
        (B) LOCATION: 15..32
        (D) OTHER INFORMATION: /note= "between nucleotides 23 and
            24 is a restriction fragment of unknown sequence."

(xi) SEQUENCE DESCRIPTION: SEQ ID NO:84:

NNNNNNNNNN NNNNGATCCC GAGTTCCGGA TCNNNNNNNN NNNNNN                    46

(2) INFORMATION FOR SEQ ID NO:85:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:85:

NNNNNNNNNN NNNNGATCCC GAGTTGCGGA TCNNNNNNNN NNNNNN                    46

(2) INFORMATION FOR SEQ ID NO:86:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..23

```
            (D) OTHER INFORMATION: /note= "Restriction fragment after
                nucleotide 23."

(xi) SEQUENCE DESCRIPTION: SEQ ID NO:86:

NNNNNNNNNN NNNNGATCCC GAG                                                23

(2) INFORMATION FOR SEQ ID NO:87:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..23
        (D) OTHER INFORMATION: /note= "Restriction fragment after
            nucleotide 23."

(xi) SEQUENCE DESCRIPTION: SEQ ID NO:87:

NNNNNNNNNN NNNNCTAGGG CTC                                                23

(2) INFORMATION FOR SEQ ID NO:88:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..23
        (D) OTHER INFORMATION: /note= "Restriction fragment before
            nucleotide 1."

(xi) SEQUENCE DESCRIPTION: SEQ ID NO:88:

TTGCGGATCN NNNNNNNNNN NNN                                                23

(2) INFORMATION FOR SEQ ID NO:89:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..23
        (D) OTHER INFORMATION: /note= "Restriction fragment before
            nucleotide 1."

(xi) SEQUENCE DESCRIPTION: SEQ ID NO:89:

AACGCCTAGN NNNNNNNNNN NNN                                                23

(2) INFORMATION FOR SEQ ID NO:90:

(i) SEQUENCE CHARACTERISTICS:
        (A) LENGTH: 24 base pairs
        (B) TYPE: nucleic acid
        (C) STRANDEDNESS: double
        (D) TOPOLOGY: linear
```

-continued

```
    (ii) MOLECULE TYPE: DNA (genomic)

(xi) SEQUENCE DESCRIPTION: SEQ ID NO:90:

TCCGGATCCG AAGACGGATC CTAA                                              24
```